United States Patent
Raheem et al.

(10) Patent No.: US 10,745,428 B2
(45) Date of Patent: Aug. 18, 2020

(54) ANTIVIRAL PHOSPHODIAMIDE PRODRUGS OF TENOFOVIR

(71) Applicants: Merck Sharp & Dohme Corp., Rahway, NJ (US); Idenix Pharmaceuticals LLC, Cambridge, MA (US)

(72) Inventors: Izzat Tiedje Raheem, Doylestown, PA (US); Timothy J. Hartingh, Richlandtown, PA (US); John Schreier, Harleysville, PA (US); Jean-Laurent Paparin, Montpellier (FR)

(73) Assignees: IDENIX PHARMACEUTICALS LLC, Cambridge, MA (US); MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 15/781,985

(22) PCT Filed: Dec. 5, 2016

(86) PCT No.: PCT/US2016/064883
§ 371 (c)(1),
(2) Date: Jun. 6, 2018

(87) PCT Pub. No.: WO2017/100108
PCT Pub. Date: Jun. 15, 2017

(65) Prior Publication Data
US 2018/0362562 A1  Dec. 20, 2018

(30) Foreign Application Priority Data
Dec. 10, 2015 (EP) .................. 15306977

(51) Int. Cl.
*A61K 31/675* (2006.01)
*C07F 9/6561* (2006.01)
*A61P 31/18* (2006.01)
*A61K 45/06* (2006.01)

(52) U.S. Cl.
CPC ........ *C07F 9/65616* (2013.01); *A61K 31/675* (2013.01); *A61K 45/06* (2013.01); *A61P 31/18* (2018.01)

(58) Field of Classification Search
CPC ...... C07F 9/65616; A61P 31/18; A61K 45/06; A61K 31/675
USPC ........................................ 514/81
See application file for complete search history.

(56) References Cited

U.S. PATENT DOCUMENTS

| | | | |
|---|---|---|---|
| 5,935,946 A | 8/1999 | Munger, Jr. et al. | |
| 5,977,089 A | 11/1999 | Arimilli et al. | |
| 7,390,791 B2 | 6/2008 | Becker et al. | |
| 7,553,825 B2 | 6/2009 | Cheng et al. | |
| 8,088,754 B2 | 1/2012 | Cheng et al. | |
| 8,268,802 B2 | 9/2012 | Cheng et al. | |
| 8,754,065 B2 | 6/2014 | Liu et al. | |
| 9,822,138 B2 | 11/2017 | Vachal et al. | |
| 2009/0202484 A1 | 8/2009 | Chong et al. | |
| 2009/0232768 A1 | 9/2009 | Birkus et al. | |
| 2015/0225433 A1 | 8/2015 | Zhang et al. | |
| 2016/0083407 A1 | 3/2016 | Hostetler et al. | |
| 2017/0044192 A1 | 2/2017 | Vachal et al. | |
| 2018/0179208 A1 | 6/2018 | Paparin et al. | |

FOREIGN PATENT DOCUMENTS

| CN | 106167504 | 11/2016 |
|---|---|---|
| EP | 2891658 A1 | 7/2015 |
| WO | 199507920 | 3/1995 |
| WO | 200147935 A1 | 7/2001 |
| WO | 2007002912 A2 | 1/2007 |
| WO | 2008005555 A1 | 1/2008 |
| WO | 2011123586 A1 | 10/2011 |
| WO | 2011140640 A1 | 11/2011 |

(Continued)

OTHER PUBLICATIONS

Wikipedia, Management of HIV/AIDS, Jan. 2015, p. 1-21 (Year: 2015).*
Aitipamula, S., et al, "Polymorphs, Salts, and Cocrystals: What's in a Name", Crystal Growth and Design, 2012, pp. 2147-2152, vol. 12.
Cesnek, M., et al.,, "Bisamidate Prodrugs of 2-Substituted 9-[2-(Phosphonomethoxy) Ethyl]Adenine (PMEA, adefovir) as Selective Inhibitors of Adenylate Cyclase Toxin From Bordetella Pertussis", Chem. Med. Chem., 2015, pp. 1531-1364, 10.

(Continued)

*Primary Examiner* — Taylor V Oh
(74) *Attorney, Agent, or Firm* — Eric Meade; John C. Todaro

(57) ABSTRACT

Compounds of Formula I and pharmaceutically acceptable salts and co-crystals thereof are useful for the inhibition of HIV reverse transcriptase. The compounds may also be useful for the prophylaxis or treatment of infection by HIV and in the prophylaxis, delay in the onset or progression, and treatment of AIDS. The compounds and their salts can be employed as ingredients in pharmaceutical compositions, optionally in combination with other antiviral agents, immunomodulators, antibiotics or vaccines.

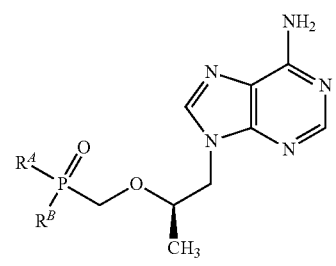

4 Claims, No Drawings

(56) References Cited

FOREIGN PATENT DOCUMENTS

| WO | 2013095684 A1 | 6/2013 |
|---|---|---|
| WO | 2017007701 A1 | 1/2017 |
| WO | 2017027434 A1 | 2/2017 |
| WO | 2017106069 A1 | 6/2017 |
| WO | 2018039157 A1 | 3/2018 |
| WO | 2018080903 A1 | 5/2018 |
| WO | 2018118826 A1 | 6/2018 |

OTHER PUBLICATIONS

Derudas, M., et al, "The Application of Phosphoramidate Protide Technology to Acyclovir Confers Anti-HIV Inibition", J. Med. Chem., 2009, pp. 5520-5530, vol. 52.

Jansa, P., et al, "A Novel and Efficient One-Pot Synthesis of Symmetrical Diamide (bis-amidate) Prodrugs of Acyclic Nucleoside Phosphonates and Evaluation of Their Biological Activites", European Journal of Medicinal Chemistry, 2011, pp. 3748-3754, Vo. 46.

Kesisoglou, F, et al, "Nanosizing—Oral Formulation Developement and Biopharmaceutical Evaluation", Adv. Drug Delivery, 2007, pp. 631-644, vol. 59, No. 7.

Martin, A., et al, Simplification of Antiretroviral Therapy, Clinical Infectious Diseases, 2009, pp. 1591-1601, vol. 49.

Pertusati, F., et al.,, "PMPA and PMEA Prodrugs for the Treatment of HIV Infections and Human Papillomavius (HPV) Associated Neoplasia and Cancer", European Journal of Medicinal Chemistry, Mar. 17, 2014, pp. 259-268, vol. 78.

Petr, et al., A novel and efficient one-pot synthesis of symmetrical diamide (bis-amidate) prodrugs of acyclic nucleoside phosphonates and evaluation of their biological activities, European Journal of Medicinal Chemistry, Editions Scientifique Elsevier, May 14, 2011, pp. 3748-3754, vol. 46, No. 9.

PubChem, Compound Summary for CID 86580209, Jan. 21, 2015.

Ray, A.S., et al.,, "Tenofovir Alafenamide: A Novel Prodrug of Tenofovir for the Treatment of Human Immunodeficiency Virus", Antiviral Research, 2016, pp. 63-70, vol. 125.

Roche, E.B., Bioreversible Carriers in Drug Design, Theory and Application, Pergamon Press, 1987.

Serajuddin, A., et al.,, "Solid Dispersion of Poorly Water-Soluble Drugs: Early Promises, Subsequent Problems, and Recent Breakthroughs", J. Pharm Sci., 1999, pp. 1058-1066, vol. 88, No. 10.

Higuchi, T., et al, "Pro-drugs as Novel Delivery Systems", A.C.S. Symposium Series, 1987, 14, pp. 1-6.

Wang et al., Assessment of the susceptibility of mutant HIV-1 to antiviral agents, Journal of Virological Methods, 2010, pp. 230-237, 165(2).

Amino-Acids Reference Chart (2009) http://www.sigmaaldrich.com/life-science/metabolomics/learning-center/amino-acid-reference-chart.html.

Cahard, D., et al, "Aryloxy Phosphoramidate Triesters As Pro-Tides", Mini-Reviews in Medicinal Chemistry, 2004, pp. 371-381, vol. 4.

Cheng, R.P., et al.,, "B-Peptides: From Structure to Function", Chem. Rev., 2001, pp. 3219-3232, vol. 101, No. 10.

Cihlar, T., et al, "Nucleoside and Nucleotide HIV Reverse Transcriptase Inhibitors: 25 years After Zidovudine", Antiviral Research, 2010, pp. 39-58, vol. 85, No. 1, EP.

Mayo Clinic. HIV/AIDS. Prevention. (2015) Web http://www.mayoclinic.org/diseases-conditions/hiv-aids/basics/prevention/con-20013732.

McGuigan, C., "Phosphorodiamidates as a Promising New Phosphate Prodrug Motif for Antiviral Drug Discovery: Application to Anti-HCV Agents", Journal of Medicinal Chemistry, 2011, pp. 8632-8645, vol. 54.

McGuigan, C., et al, "Design, Synthesis and Biologial Evaluation of Phosphorodiamidate Prodrugs of Antiviral and Anticancer Nucleosides", European Journal of Medicinal Chemistry, 2013, pp. 326-340, vol. 70.

Pradere, U., et al, "Synthesis of Nucleoside Phosphate and Phosphonate Prodrugs", Chemical Reviews, 2014, pp. 9154-9218, vol. 114, No. 18.

Smidkova, Marketa, "Amidate Prodrugs of 9-[2(Phosphonomethoxy)Ethyl[Adenine as Inhibitors of Adenylate Cyclase Toxin From Bordetella Pertussis", Antimicrobial Agents and Chemotherapy, 2014, pp. 664-671, vol. 58, No. 2.

* cited by examiner

ANTIVIRAL PHOSPHODIAMIDE PRODRUGS OF TENOFOVIR

RELATED APPLICATIONS

This application claims priority to EP Application No. EP15306977.8 filed Dec. 10, 2015 and to PCT/US2016/064883 filed Dec. 5, 2016. Each of the aforementioned applications to which this application claims priority is herein incorporated by reference in its entirety.

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. During the viral RNA-dependent polymerization process, RT's ribonuclease activity is required for removing RNA and leaving the polypurine tract preserved for initiation of DNA-dependent polymerization. As a DNA-dependent DNA polymerase, RT makes a second, complementary DNA strand using the first DNA strand as a template. The two strands form double-stranded DNA, which is integrated into the host cell's genome by HIV integrase.

It is known that compounds that inhibit enzymatic functions of HIV RT will inhibit HIV replication in infected cells. These compounds are useful in the treatment of HIV infection in humans. There are two classes of RT inhibitors: one is non-nucleoside active site competitive RT inhibitors (NNRTIs), such as efavirenz (EFV), nevirapine (NVP), etravirine (ETR), and rilpivirine (RPV), and the other is active site RT inhibitors which include nucleoside reverse transcriptase inhibitors (NsRTIs) and nucleotide reverse transcriptase inhibitors (NtRTIs), collectively referred to as NRTIs. Examples of NsRTI's include 3'-azido-3'-deoxythymidine (AZT), 2',3'-dideoxyinosine (ddI), 2',3'-dideoxycytidine (ddC), 2',3'-didehydro-2',3'-dideoxythymidine (d4T), 2',3'-dideoxy-3'-thiacytidine (3TC), abacavir, and emtricitabine. Examples of NtRTIs include tenofovir (TFV, also known as PMPA, 9-(2-phosphonyi-methoxypropyl)adenine), tenofovir disoproxil fumarate (VIREAD®, U.S. Pat. Nos. 5,977,089, 5,935,946) and tenofovir alafenamide fumarate (U.S. Pat. Nos. 7,390,791, 8,754,065).

TFV belongs to a class of HIV anti-retroviral (ARV) agents known as nucleotide analog reverse transcriptase inhibitors (NRTIs). Tenofovir is a monophosphonate:

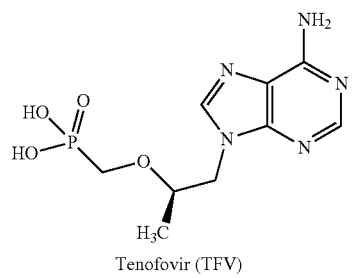 [SMILES: C[C@H](Cn1cnc2c(N)ncnc21)OCP(=O)(O)O]

Tenofovir (TFV)

After ebing taken up by cells, TFV is first converted to tenofovir-monophosphate (TFV-MP) by adenosine monophosphate kinase and then to the active antiviral tenofovir-diphosphate (TFV-DP) by 5'-nucleoside diphosphate kinase.

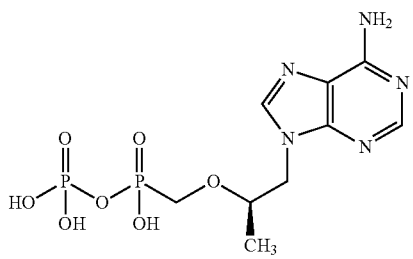

Tenofovir-monophosphate (TFV-MP)

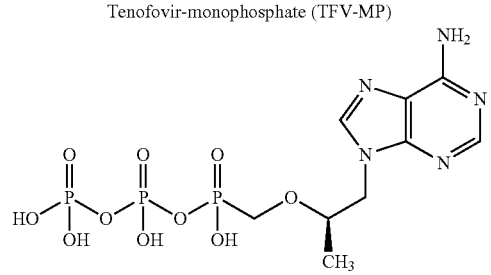

Tenofovir-diphosphate (TFV-DP)

TFV-DP inhibits HIV DNA synthesis by competing with the natural substrate, deoxyadenosine triphosphate, for incorporation into the complementary DNA strand by HIV to reverse transcriptase; following incorporation, TFV acts as a chain terminator due to lack of a 3'-hydroxyl group that is required for addition of the next nucleotide. TFV has poor cellular permeability and thus has limited bioavailability. Tenofovir disoproxil fumarate (TDF) is approved for treating HIV infection and is marketed by Gilead under the trade name VIREAD™. The disoproxil prodrug improves cell permeability and absorption after oral dosing, with the pro-moiety being cleaved rapidly after absorption to yield the parent TFV. As a result, the circulating level of TFV is much higher than that of TDF. Tenofovir alafenamide fumarate (TAF) is currently approved by the USFDA as an active ingredient in combination with additional ARVs for treating HIV infection in the pharmaceutical products GENVOYA®, ODEFSEY® and DESCOVY®.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of RT inhibitors to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a particular need for new RT inhibitors that are effective against mutant HIV strains.

SUMMARY OF THE INVENTION

The present invention is directed to phosphodiamide prodrugs of tenofovir and their use in the inhibition of nucleotide reverse transcriptase. In addition to the use of said compounds in the inhibition of HIV reverse transcriptase, the invention is also directed to the use of said compounds for prophylaxis of infection by HIV, the treatment of infection by HIV, and the prophylaxis, treatment, and/or delay in the onset or progression of AIDS and/or ARC. The invention also encompasses methods of using said compounds for the treatment of chronic hepatitis B infection.

DETAILED DESCRIPTION OF TI-IE INVENTION

The present invention is directed to compounds of structural Formula I:

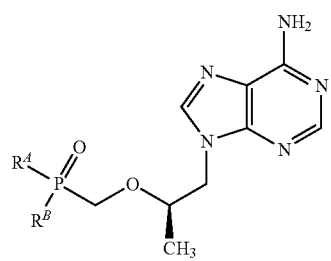

or pharmaceutically acceptable salts thereof, wherein:
$R^A$ is a D-amino acid ester residue of formula (i) or a D-proline ester residue of formula (ii):

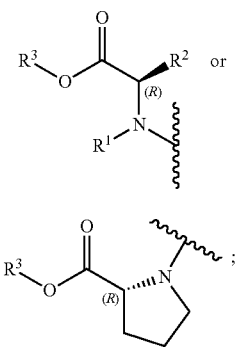

$R^1$ is (a) H, or (b) —$C_{1-3}$alkyl optionally substituted with one to three substituents independently selected from fluoro, chloro, bromo, and —OH;
$R^2$ is (a) H, (b) —$C_{1-4}$alkyl, (c) —$C_{1-4}$alkyl substituted with —OH, —SH, —SCH$_3$, —NH$_2$ or —NH—C(=NH)—NH$_2$, (d) —CH$_2$-phenyl, (e) —CH$_2$-phenol, (f) —(CH$_2$)$_{1-2}$—COOH, (g) —(CH$_2$)$_{1-2}$—CONH$_2$, (h) —CH$_2$-1H-indole, (i) —CH$_2$-imidazole, (j) aryl (for example but not limited to phenyl or naphthyl) or (k) heteroaryl (for example but not limited to pyridine);
$R^3$ is
(a) —$C_{1-10}$alkyl unsubstituted or substituted with one to three substituents independently selected from fluoro, chloro, bromo, —OR$^7$, —SH, —NR$^8$R$^9$, —$C_{3-6}$cycloalkyl or spiro—$C_{3-6}$cycloalkyl,
(b) —CH$_2$-phenyl unsubstituted or substituted with one to three substituents independently selected from fluoro, chloro, bromo, —OR$^{10}$, —SH, —NR$^8$R$^9$ or —$C_{1-3}$alkyl,
(c) —$C_{3-8}$cycloalkyl unsubstituted or substituted with one to three substituents independently selected from fluoro, chloro, bromo, —OR$^{10}$, —SH, —NR$^8$R$^9$ or —$C_{1-3}$alkyl,
(d) aryl unsubstituted or substituted with one to three substituents independently selected from fluoro, chloro, bromo, —OR$^{10}$, —SH, —NR$^8$R$^9$ or —$C_{1-3}$alkyl,
(e) —$C_{1-5}$alkyl-X—$C_{1-5}$alkyl wherein X is O, S, or NH,
(f) heteroaryl unsubstituted or substituted with one to three substituents independently selected from fluoro, chloro, bromo, —OR$^{10}$, —SH, —NR$^8$R$^9$ or —$C_{1-3}$alkyl, or
(g) a heterocyclic ring unsubstituted or substituted with one to three substituents independently selected from fluoro, chloro, bromo, —OR$^{10}$, —SH, —NR$^8$R$^9$ or —$C_{1-3}$alkyl;
$R^B$ is a geminally di-substituted amino acid ester residue of formula (iii):

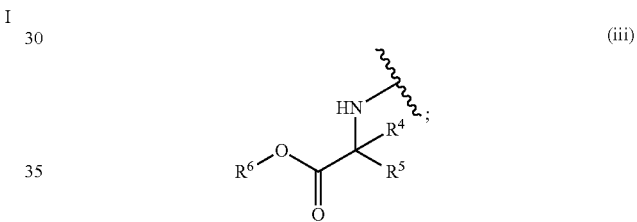

$R^4$ and $R^5$ are each independently selected from (a) —$C_{1-4}$alkyl, (b) —$C_{1-4}$alkyl substituted with —OH, —SH, —SCH$_3$, —NH$_2$, —NH—C(=NH)—NH$_2$, (c) —CH$_2$-phenyl, (d) —CH$_2$phenol, (e) —(CH$_2$)$_{1-2}$—COOH, (f) —(CH$_2$)$_{1-2}$CONH$_2$, (g) —CH$_2$-1H-indole, (h) —CH$_2$-imidazole, (i) aryl (for example but not limited to phenyl or naphthyl) or (j) heteroaryl (for example but not limited to pyridine); or $R^4$ and $R^5$ are joined together with the carbon to which they are both attached to form —$C_{3-6}$cycloalkyl or a 4 to 6-membered heterocyclic ring;
$R^6$ is
(a) —$C_{1-10}$alkyl unsubstituted or substituted with one to three substituents independently selected from fluoro, chloro, bromo, —OR$^{11}$, —SH, —NR$^{12}$R$^{13}$, —$C_{3-6}$cycloalkyl or spiro-$C_{3-6}$cycloalkyl,
(b) —CH$_2$-phenyl unsubstituted or substituted with one to three substituents independently selected from fluoro, chloro, bromo, —OR$^{14}$, —SH, —NR$^{12}$R$^{13}$ or —$C_{1-3}$alkyl,
(c) —$C_{3-8}$cycloalkyl unsubstituted or substituted with one to three substituents independently selected from fluoro, chloro, bromo, —OR , —SH, —NR$^{12}$R$^{13}$ or —$C_{1-3}$alkyl,
(d) aryl unsubstituted or substituted with one to three substituents independently selected from fluoro, chloro, bromo, —OR , —SH, —NR$^{12}$R$^{13}$ or —$C_{1-3}$alkyl,
(e) —$C_{1-5}$alkyl-X—$C_{1-5}$alkyl wherein X is O, S or NH;
(f) heteroaryl unsubstituted or substituted with one to three substituents independently selected from fluoro, chloro, bromo, —OR$^{14}$, —SH, —NR$^{12}$R$^{13}$ or —$C_{1-3}$alkyl, or (g) a heterocyclic ring unsubstituted or substituted with one to three substituents independently selected from fluoro, chloro, bromo, —OR$^{14}$, —SH, —NR$^{12}$R$^{13}$ or —C$_{1-3}$alkyl;

R$^7$ and R$^{11}$ are each independently selected from —H or —C$_{3-6}$cycloalkyl;

R$^8$ and R$^9$ are each independently selected from —H, —C$_{1-3}$alkyl or —C$_{3-6}$cycloalkyl;

R$^{12}$ and R$^{13}$ are each independently selected from —H, —C$_{1-3}$alkyl or —C$_{3-6}$cycloalkyl; and R$^{10}$ and R$^{14}$ are each independently selected from —H, —C$_{1-3}$alkyl or —C$_{3-6}$cycloalkyl.

In an embodiment of this invention are compounds of Formula I or the pharmaceutically acceptable salts thereof, wherein R$^4$ is formula (i):

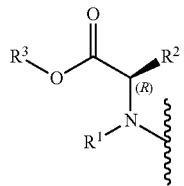

(i)

referred to herein as compounds of Formula I-i;
and the remaining variables are as defined in Formula I.

In an embodiment of this invention are compounds of Formula I or the pharmaceutically acceptable salts thereof, wherein R$^4$ is formula (ii):

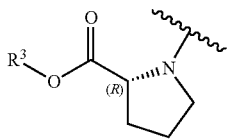

(ii)

referred to herein as compounds of Formula I-ii;
and the remaining variables are as defined in Formula I.

In Embodiment 1 of this invention are compounds of Formula I, I-i, or I-ii, or Embodiment 2, 2a, 3, 4, 4a, 5, 6, 7, 8, 9 or 10 or a class thereof, or the pharmaceutically acceptable salts thereof, wherein if present (as in Formula I-i) R$^1$ is H or —C$_{1-4}$alkyl and R$^2$ is H or —C$_{1-4}$alkyl; and the remaining variables are as defined in Formula I. In a class thereof, one of R$^1$ and R$^2$ is H, and the other is H or —C$_{1-4}$alkyl; and in a sub-class thereof one of R$^1$ and R$^2$ is H, and the other is —C$_{1-4}$alkyl, for example methyl or i-propyl. In a class thereof, R$^1$ is H or —C$_{1-4}$alkyl and R$^2$ is —C$_{1-4}$alkyl. In a sub-class thereof, R$^1$ is H and R$^2$ is methyl. In a sub-class thereof, R$^1$ is methyl and R$^2$ is methyl.

In Embodiment 2 of this invention are compounds of Formula I, or I-ii or Embodiment 1, or the pharmaceutically acceptable salts thereof, wherein R$^3$ is
(a) —C$_{1-8}$alkyl, —CH$_2$CH$_2$OH, —CH$_2$CH$_2$CH$_2$OH, —CH$_2$CH$_2$SH, —CH$_2$CH$_2$CH$_2$SH, —CH$_2$CH$_2$NH$_2$, or —CH$_2$CH$_2$CH$_2$NH$_2$,
(b) —CH$_2$-phenyl, unsubstituted or substituted with one to three substituents independently selected from fluoro, chloro, bromo, —OR$^{10}$, —SH, —NR$^8$R$^9$ or —C$_{1-3}$alkyl,
(c) —C$_{3-6}$cycloalkyl, unsubstituted or substituted with one to three substituents independently selected from fluor, chloro, bromo, —OR$^{10}$, —SH, —NR$^8$R$^9$ or —C$_{1-3}$alkyl,
(d) phenyl or naphthyl, each unsubstituted or substituted with one to three substituents independently selected from fluoro, chloro, bromo, —OR$^{10}$, —SH, —NR$^8$R$^9$ or —C$_{1-3}$alkyl,
(e) —CH$_2$CH$_2$OCH$_3$, —CH$_2$CH$_2$CH$_2$OCH$_3$, —CH$_2$CH$_2$SCH$_3$, —CH$_2$CH$_2$CH$_2$SCH$_3$, —CH$_2$CH$_2$NHCH$_3$, —CH$_2$CH$_2$CH$_2$NHCH$_3$,
(f) pyridyl, unsubstituted or substituted with one to three substituents independently selected from fluoro, chloro, bromo, —OR$^{10}$, —SH, —NR$^8$R$^9$ or —C$_{1-3}$alkyl, or
(g) piperidinyl, pyrrolidinyl, tetrahydrofuranyl, or tetrahydropyranyl, each unsubstituted or substituted with one to three substituents independently selected from fluoro. chloro, bromo, —OR$^{10}$, —SH, —NR$^8$R$^9$ or —C$_{1-3}$alkyl;
and the remaining variables are as defined in Formula I.

In a class of Embodiment 2, referred to as Embodiment 2a, R$^3$ is cyclopropyl, cyclobutyl, cyclopentyl or cyclohexyl, and in a sub-class thereof, R$^3$ is —C$_{3-8}$alkyl, for example i-propyl; and the remaining variables are as defined in Formula I.

In Embodiment 3 of this invention are compounds of Formula I, I-i or I-ii or Embodiment 1, 2 or 2a, or the pharmaceutically acceptable salts thereof, wherein R$^4$ and R$^5$ are each independently selected from —CH$_3$, —CH$_2$CH$_3$, —C$_3$alkyl or —C$_4$alkyl; and the remaining variables are as defined in Formula I. In another class of Embodiment 3, R$^4$ and R$^5$ are both the same atom moiety which is selected from —CH$_3$, —CH$_2$CH$_3$, —C$_3$alkyl or —C$_4$alkyl; and in a sub-class thereof R$^4$ and R$^5$ are both —CH$_3$.

In Embodiment 4 of this invention are compounds of Formula I, I-i or I-ii or Embodiment 1, 2, 2a or 3, or the pharmaceutically acceptable salts thereof, wherein R$^6$ is
(a) —C$_{1-8}$alkyl, —CH$_2$CH$_2$OH, —CH$_2$CH$_2$CH$_2$OH, —CH$_2$CH$_2$SH, —CH$_2$CH$_2$CH$_2$SH, —CH$_2$CH$_2$NH$_2$, —CH$_2$CH$_2$CH$_2$NH$_2$.
(b) —CH$_2$-phenyl, unsubstituted or substituted with one to three substituents independently selected from fluoro, chloro, bromo —OR$^{14}$, —SH, —NR$^{12}$R$^{13}$ or —C$_{1-3}$alkyl,
(c) —C$_{3-6}$cycloalkyl, unsubstituted or substituted with one to three substituents independently selected from fluoro, chloro, bromo, —OR$^{14}$, —SH, —NR$^{12}$R$^{13}$ or —C$_{1-3}$alkyl,
(d) phenyl or naphthyl, each unsubstituted or substituted with one to three substituents independently selected from fluoro, chloro, bromo, —OR$^{14}$, —SH, —NR$^{12}$R$^{13}$ or —C$_{1-3}$alkyl,
(e) —CH$_2$CH$_2$OCH$_3$, —CH$_2$CH$_2$CH$_2$OCH$_3$, —CH$_2$CH$_2$SCH$_3$, —CH$_2$CH$_2$CH$_2$SCH$_3$, —CH$_2$CH$_2$NHCH$_3$, —CH$_2$CH$_2$CH$_2$NHCH$_3$,
(f) pyridyl, unsubstituted or substituted with one to three substituents independently selected from fluoro, chloro, bromo, —OR$^{14}$, —SH, —NR12R$^{13}$ or —C$_{1-3}$alkyl, or
(g) piperidinyl, pyrrolidinyl, tetrahydrofuranyl, or tetrahydropyranyl, each unsubstituted or substituted with one to three substituents independently selected from fluoro, chloro, bromo, —OR$^{14}$, —SH, —NR$^{12}$R$^{13}$ or —C$_{1-3}$alkyl;
and the remaining variables are as defined in Formula I.

In a class of Embodiment 4, referred to as Embodiment 4a, R$^6$ is —C$_{1-8}$alkyl, cyclopropyl, cyclobutyl, cyclopentyl or cyclohexyl, and in a sub-class thereof R$^6$ is —C$_{3-8}$alkyl, cyclobutyl, cyclopentyl or cyclohexyl; and the remaining variables are as defined in Formula I.

In Embodiment 5 of this invention are compounds of Formula I, or a pharmaceutically acceptable salt thereof, wherein:

$R^1$, is present (as in Formula I-i), is H or —$C_{1-4}$alkyl;
$R^2$, if present (as in Formula I-i), is H or —$C_{1-4}$alkyl;
$R^3$ is
(a) —$C_{1-8}$alkyl, —$CH_2CH_2OH$, —$CH_2CH_2CH_2OH$, —$CH_2CH_2SH$, —$CH_2CH_2CH_2SH$, —$CH_2CH_2NH_2$, —$CH_2CH_2CH_2NH_2$,
(b) —$CH_2$-phenyl, unsubstituted or substituted with one to three substituents independently selected from fluoro, chloro, bromo, —$OR^{10}$, —SH, —$NR^8R^9$ or —$C_{1-3}$alkyl,
(c) —$C_{3-6}$cycloalkyl, unsubstituted or substituted with one to three substituents independently selected from fluoro, chloro, bromo, —$OR^{10}$, —SH, —$NR^8R^9$ or —$C_{1-3}$alkyl,
(d) phenyl or naphthyl, each unsubstituted or substituted with one to three substituents independently selected from fluoro, chloro, bromo, —$OR^{10}$, —SH, —$NR^8R^9$ or —$C_{1-3}$alkyl,
(e) —$CH_2CH_2OCH_3$, —$CH_2CH_2CH_2OCH_3$, —$CH_2CH_2SCH_3$, —$CH_2CH_2CH_2SCH_3$, —$CH_2CH_2NHCH_3$, —$CH_2CH_2CH_2NHCH_3$,
(f) pyridyl, unsubstituted or substituted with one to three substituents independently selected from fluoro, chloro, bromo, —$OR^{10}$, —SH, —$NR^8R^9$ or —$C_{1-3}$alkyl, or
(g) piperidinyl, pyrrolidinyl, tetrahydrofuranyl, or tetrahydropyranyl, each unsubstituted or substituted with one to three substituents independently selected from fluoro, chloro, bromo, —$OR^{10}$, —SH, —$NR^8R^9$ or —$C_{1-3}$alkyl, or
$R^4$ and $R^5$ are both the same moiety which is selected from —$CH_3$, —$CH_2CH_3$, —$C_3$alkyl or —$C_4$alkyl;
$R^6$ is
(a) —$CH_{1-8}$alkyl, —$CH_2CH_2OH$, —$CH_2CH_2CH_2OH$, —$CH_2CH_2SH$, —$CH_2CH_2CH_2SH$, —$CH_2CH_2NH_2$, —$CH_2CH_2CH_2NH_2$,
(b) —$CH_2$-phenyl, unsubstituted or substituted with one to three substituents independently selected from fluoro, chloro, bromo, —$OR^{14}$, —SH, —$NR^{12}R^{13}$ or —$C_{1-3}$alkyl,
(c) —$C_{3-6}$cycloalkyl, unsubstituted or substituted with one to three substituents independently selected from fluoro, chloro, bromo, —$OR^{14}$, —SH, —$NR^{12}R^{13}$ or —$C_{1-3}$alkyl,
(d) phenyl or naphthyl, each unsubstituted or substituted with one to three substituents independently selected from fluoro, chloro, bromo, —$OR^{14}$, —SH, —$NR^{12}R^{13}$ or —$C_{1-3}$alkyl,
(e) —$CH_2CH_2OCH_3$, —$CH_2CH_2CH_2OCH_3$, —$CH_2CH_2SCH_3$, —$CH_2CH_2CH_2SCH_3$, —$CH_2CH_2NHCH_3$, —$CH_2CH_2CH_2NHCH_3$,
(f) pyridyl, unsubstituted or substituted with one to three substituents independently selected from fluoro, chloro, bromo, —$OR^{14}$, —SH, —$NR^{12}R^{13}$ or —$C_{1-3}$alkyl,
(g) piperidinyl, pyrrolidinyl, tetrahydrofuranyl, or tetrahydropyranyl, each unsubstituted or substituted with one to three substituents independently selected from fluoro, chloro, bromo, —$OR^{14}$, —SH, —$NR^{12}R^{13}$ or —$C_{1-3}$alkyl;
and the remaining variables are as defined in Formula I.

In Embodiment 6 of this invention are compounds of Formula I, I-i or I-ii, or a pharmaceutically acceptable salt thereof, wherein
$R^1$, if present (as in Formula I-i), is H or —$C_{1-4}$alkyl;
$R^2$, if present (as in Formula I-i), is —$C_{1-4}$alkyl; and
$R^3$ is —$C_{1-8}$alkyl, cyclopropyl, cyclobutyl, cyclopentyl or cyclohexyl, or in a class of Embodiment 6, $R^3$ is i-propyl;
and the remaining variables are as defined in Formula I.

In Embodiment 7 of this invention are compounds of Embodiment 6 having Formula I or I-i, or a pharmaceutically acceptable salt thereof, wherein
$R^6$ is —$C_{1-8}$alkyl, cyclopropyl, cyclobutyl, cyclopentyl or cyclohexyl, or in a class of Embodiment 7, $R^6$ is —$C_{3-8}$alkyl;
and the remaining variables are as defined in Formula I.

In Embodiment 8 of this invention are compounds of Embodiment 6 having Formula I or I-ii, or a pharmaceutically acceptable salt thereof, wherein
$R^6$ is —$C_{1-8}$alkyl, cyclopropyl, cyclobutyl, cyclopentyl or cyclohexyl, or in a class of Embodiment 8, $R^6$ is —$C_{3-8}$alkyl;
and the remaining variables are as defined in Formula I.

In Embodiment 9 of this invention are compounds of Formula I, or a pharmaceutically acceptable salt thereof, wherein:
$R^1$, if present (as in Formula I-i), is H or —$CH_3$;
$R^2$, if present (as in Formula I-i), is —$C_{1-4}$alkyl;
$R^3$ is —$C_{1-8}$alkyl, cyclopropyl, cyclobutyl, cyclopentyl or cyclohexyl;
$R^4$ and $R^5$ are both —$CH_3$;
$R^6$ is —$C_{1-8}$alkyl, cyclopropyl, cyclobutyl, cyclopentyl or cyclohexyl;
and the remaining variables are as defined in Formula I.

In Embodiment 10 of this invention are compounds of Formula I, or a pharmaceutically acceptable salt thereof, wherein:
$R^1$, if present (as in Formula I-i), is H or —$CH_3$;
$R^2$, if present (as in Formula I-i), is —$C_{1-4}$alkyl;
$R^3$ is —$C_{3-8}$alkyl, cyclobutyl, cyclopentyl or cyclohexyl;
$R^4$ and $R^5$ are both —$CH_3$;
$R^6$ is —$C_{3-8}$alkyl, cyclobutyl, cyclopentyl or cyclohexyl;
and the remaining variables are as defined in Formula I.

In Embodiment 11 of this invention are compounds of Formula I, or a pharmaceutically acceptable salt thereof, wherein:
$R^1$, if present (as in Formula I-i), is H or —$CH_3$;
$R^2$, if present (as in Formula I-i), is —$C_{1-4}$alkyl;
$R^3$ is —$C_{3-8}$alkyl, or in a class of Embodiment 11, $R^3$ is i-propyl;
$R^4$ and $R^5$ are both —$CH_3$;
$R^6$ is —$C_{3-8}$alkyl, cyclobutyl, cyclopentyl or cyclohexyl;
and the remaining variables are as defined in Formula I.

In Embodiment 12 of this invention are compounds of Formula I, or a pharmaceutically acceptable salt thereof, wherein:
$R^1$, if present (as in Formula I-i), is H or —$CH_3$;
$R^2$, if present (as in Formula I-i), is —$C_{1-4}$alkyl;
$R^3$ is —$C_{3-8}$alkyl, cyclobutyl, cyclopentyl or cyclohexyl;
$R^4$ and $R^5$ are both —$CH_3$;
$R^6$ is —$C_{3-8}$alkyl;
and the remaining variables are as defined in Formula I.

Reference to the compounds of Formula I herein encompasses the compounds of Formula I and all embodiments, classes and sub-classes thereof. The compounds of the invention encompass compounds of Formula I and salts thereof when such salts are possible, including pharmaceutically acceptable salts.

As used herein, "alkyl" refers to both branched-and straight-chain saturated aliphatic hydrocarbon groups having the specified number of carbon atoms in a specified range. For example the term "$C_{1-10}$alkyl" means linear or branched chain alkyl groups, including all possible isomers, having 1, 2, 3, 4, 5, !, 8, 9 or 10 carbon atoms, and includes each of the decyl, nonyl, octyl, heptyl, hexyl and pentyl isomers as well as n-, iso-, sec-and tert-butyl (butyl, s-butyl, i-butyl, t-butyl; Bu=butyl, collectively "—C$_4$alkyl"), n-and iso-propyl (propyl, i-propyl, Pr=propyl, collectively "—C$_3$alkyl"), ethyl (Et) and methyl (Me), "C$_{1-4}$alkyl" has 1, 2, 3 or 4 carbon atoms, and includes each of n-, iso-, sec-and tert-butyl, n-and i-propyl, ethyl and methyl.

"Cycloalkyl" refers to a cyclized alkyl ring having the indicated number of carbon atoms in a specified range. Thus, for example, "C$_{3-8}$ cycloalkyl" encompasses each of cyclopropyl, cyclobutyl, cyclopentyl, cyclohexyl, cyloheptyl and cyclooctyl. "C$_{3-6}$cycloalkyl" encompasses each of cyclopropyl, cyclobutyl, cyclopentyl and cyclohexyl. When cycloalkyl is a substituent on an alkyl group in a compound of Formula 1, the cycloalkyl substituent can be bonded to any available carbon in the alkyl group. The following are illustrations of —C$_{3-6}$cycloalkyl substituents wherein the substituent is cyclopropyl in bold:

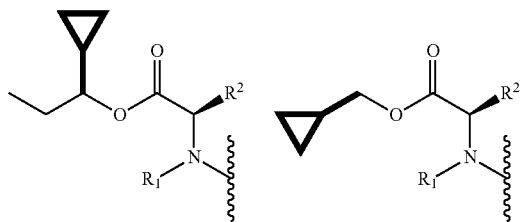

"Spiro-C$_{3-6}$cycloalkyl" refers to a cycloalkyl ring bonded to a non-terminal carbon atom wherein the non-terminal carbon atom is shared with the cycloalkyl group. Spiro-C$_{3-6}$cycloalkyl encompasses each of spiro-cyclopropyl, spiro-cyclobutyl, spiro-cyclopentyl and spiro-cyclohexyl. The following is an illustration of a spino-C$_{3-6}$cycloalkyl substituent wherein the substituent is spino-cyclopropyl in bold:

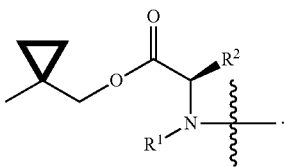

Examples of —C$_{1-5}$alkyl-X—C$_{1-5}$alkyl groups include, but are not limited to, —CH$_2$CH$_2$OCH$_3$, —CH$_2$CH$_2$CH$_2$OCH$_3$, —CH$_2$CH$_2$SCH$_3$, —CH$_2$CH$_2$CH$_2$SCH$_3$, —CH$_2$CH$_2$NHCH$_3$ or —CH$_2$CH$_2$CH$_2$NHCH$_3$.

"Aryl" refers to (i) phenyl, (ii) 9-or 10-membered bicyclic, fused carbocylic ring systems in which at least one ring is aromatic, and (iii) 11-to 14-membered tricyclic, fused carbocylic ring systems in which at least one ring is aromatic. Suitable aryls include, for example, substituted and unsubstituted phenyl and substituted and unsubstituted naphthyl. An aryl of particular interest is unsubstituted or substituted phenyl.

"Heteroaryl" refers to (i) a 5-or 6-membered heteroaromatic ring containing from 1 to 4 heteroatoms independently selected from N, O and S, wherein each N is optionally in the form of an oxide, and (ii) a 9-or 10-membered bicyclic fused ring system, wherein the fused ring system of (ii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or S(O)$_2$. Examples of 5—membered heteroaromatic rings include, but are not limited to, pyrrolyl, pyrazolyl, triazolyl (i.e., 1,2,3-triazolyl or 1,2,4-triazolyl), imidazolyl, tetrazolyl, furanyl, furanonyl (e.g., furan-2(5H)-one), thienyl, thiazolyl, isothiazolyl, oxazolyl, isooxazolyl, oxadiazolyl (i.e., the 1,2,3-, 1,2,4-, 1,2,5-(furazanyl), or 1,3,4-oxadiazolyl isomer), oxatriazolyl, and thiadiazolyl. Examples of 6-membered heteroaromatic rings include, but are not limited to, pyridyl (also referred to as pyridinyl), pyrimidinyl, pyrazinyl, pyridazinyl, and triazinyl. Examples of 9-and 10-membered heteroaromatic bicyclic fused ring systems include, but are not limited to, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, isoindolyl, benzopiperidinyl, benzofuranyl, imidazo[1,2-a]pyridinyl, benzotriazolyl, indazolyl, indolinyl, and isoindolinyl. A class of heteroaryls includes unsubstituted or substituted pyridyl or pyritnidyl, and particularly unsubstituted or substituted pyridyl.

The term "heterocyclic ring" refers to (i) a saturated 4-to 7-membered cyclized ring and (ii) an unsaturated, non-aromatic 4 to 7-membered cyclized ring comprised of carbon atoms and 1-4 heteroatoms independently selected from O, N and S. Heterocyclic rings within the scope of this invention include, for example but are not limited to, azetidinyl, piperidinyl, morpholinyl, thiomorpholinyl, thiazolidinyl, isothiazolidinyl, oxazolidinyl, isoxazolidinyl, pyrrolidinyl imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4-to 7-membered, unsaturated, non-aromatic heterocyclic rings within the scope of this invention include monounsaturated heterocyclic rings corresponding to the saturated heterocyclic rings listed in the preceding sentence in which a single bond is replaced with a double bond (e.g., a carbon-carbon single bond is replaced with a carbon-carbon double bond).

In a class of heterocyclic rings are 4 to 6-membered saturated monocyclic rings comprised of carbon atoms and 1 or 2 heteroatoms, wherein the heteroatoms are independently selected from N, O and S. Examples of 4 to 6 membered heterocyclic rings include but are not limited to, azetidinyl, pyrrolidinyl, piperidinyl piperazinyl, morpholinyl, thiomorpholinyl, tetrahydrofuranyl, tetrahydropyranyl and tetrahydrothiopyranyl, and a sub-class thereof is piperidinyl, pyrrolidinyl, tetrahydrofuranyl or tethrahdropyranyl. The following is a non-limiting illustration of R4 and R5 when they are joined together to form a heterocyclic ring:

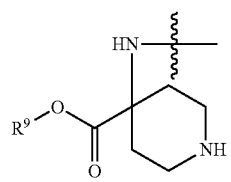

With respect to substituents on a molecule. "germinally" or "geminal" refers to two substituents, which may be the same or different, on one carbon.

It is understood that the specific rings and ring systems suitable for use in the present invention are not limited to those listed in the preceding paragraphs. These rings and ring systems are merely representative.

As would be recognized by one of ordinary skill in the art, certain compounds of the present invention maybe able to exist as tautomers. All tautomeric forms of these compounds, whether isolated individually or in mixtures, are within the scope of the present invention. For example, in instances where an —OH substituent is permitted on a heteroaromatic ring and keto-enol tautomerism is possible, it is understood that the substituent might in fact be present, in whole or in part, in the oxo (═O) form.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I and its embodiments. For example, certain moieties as defined in Formula I may be unsubstituted or substituted, and the latter is intended to encompass substitution patterns (i.e., number and kind of substituents) that are chemically possible for the moiety and that result in a stable compound.

Each compound of Formula I is comprised of a phosphodiamide amino acid ester having a defined (R) chiral center in the alkyl-ether linking group which connects the nucleobase to the phosphodiamide as shown in Formula I and may have one or more additional chiral centers depending on substituent selection. For example, each of the compounds of Examples 1-28B herein also has an asymmetric phosphorus center. Accordingly, a compound of Formula I may have multiple chiral centers (also referred to as asymmetric or stereogenic centers). This invention encompasses compounds having either the (R) or (S) stereo-configuration at a phosphorus asymmetric center and at any additional asymmetric centers that may be present in a compound of Formula I, as well as stereo-isomeric mixtures thereof.

This invention includes individual diastereomers, particularly epimers, i.e., compounds having the same chemical formula but which differ in the spatial arrangement around a single atom. This invention also includes mixtures of diastereomers, particularly mixtures of epimers, in all ratios. Embodiments of this invention also include a mixture of epimers enriched with 51% or more of one of the epimers, including for example 60% or more, 70% or more, 80% or more, or 90% or more of one epimer. A single epimer is preferred. An individual or single epimer refers to an epimer obtained by chiral synthesis and/or using generally known separation and purification techniques, and which may be 100% of one epimer or may contain small amounts (e.g., 10% or less) of the opposite epimer. Thus, individual diastereomers are a subject of the invention in pure form, both as levorotatory and as dextrorotatory antipodes, in the form of racemates and in the form of mixtures of the two diastereomers in all ratios. In the case of a cis/trans isomerism the invention includes both the cis form and the trans form as well as mixtures of these forms in all ratios.

The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I; for example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula I can he prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which is not biologically or otherwise undesirable (e.g., is neither toxic nor otherwise deleterious to the recipient thereof) Since the compounds of Formula I contain by definition at least one basic group, the invention includes the corresponding pharmaceutically acceptable salts. When the compounds of Formula I contain one or more acidic groups, the invention also includes the corresponding pharmaceutically acceptable salts. Thus, the compounds of Formula I that contain acidic groups (e.g., —COOH) can he used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I, which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

The instant invention encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design,* 2012, 12 (5), pp. 2147-2152.

More specifically with reference to this invention, a co-crystal is comprised of a compound of Formula I or a pharmaceutically acceptable salt thereof, and one or more non-pharmaceutically active component(s) which is not biologically or otherwise undesirable (e.g., is neither toxic nor otherwise deleterious to the recipient thereof). Co-crystals can be obtained from a compound of Formula I, or a pharmaceutically acceptable salt thereof, by customary methods known in the chemical arts. For example, co-crystals comprised of a compound of this invention could be prepared by adding an acid or a neutral molecule at the desired stoichiometry to the compound, adding an appropriate solvent to achieve dissolution and, for example, precipitating, lyophilizing or concentrating the solution to obtain the solid composition. The co-crystal can be, but is not limited to, an embodiment wherein the composition is comprised of a neutral compound (i.e. not a salt form) of Formula I and one or more non-pharmaceutically active component(s) and in a further embodiment, the co-crystal composition is crystalline. Crystalline compositions may be prepared, for example, by adding an acid or a neutral molecule at the desired stoichiometry to the compound of Formula I, adding an appropriate solvent and heating to achieve complete dissolution, and then allowing the solution to cool and the crystals to grow. The present invention also includes all co-crystals of the compounds of this invention which, owing to low physiological compatibility, are not directly suitable for use in pharmaceuticals but which can be used, for example, as intermediates for chemical reactions or for the preparation of pharmaceutically acceptable co-crystals or salts.

Furthermore, compounds of the present invention may exist in amorphous form and/or one or more crystalline forms, and as such all amorphous and crystalline forms and mixtures thereof of the compounds of Formula I and salts thereof are intended to be included within the scope of the present invention, In addition, some of the compounds of the instant invention may form solvates with water (i.e., a hydrate) or common organic solvents. Such solvates and hydrates, particularly the pharmaceutically acceptable solvates and hydrates, of the compounds of this invention are likewise encompassed within the scope of the compounds defined by Formula I and the pharmaceutically acceptable salts thereof, along with un-solvated and anhydrous forms of such compounds.

Accordingly, the compounds of Formula I, embodiments thereof and specific compounds described and claimed herein encompass all possible salts, including pharmaceutically acceptable salts, stereoisomers, tautomers, physical forms (e.g., amorphous and crystalline forms), co-crystal forms, solvate and hydrate forms, and any combination of the foregoing forms where such forms are possible.

The compounds of Formula I (or any embodiment thereof including pharmaceutically acceptable salts thereof) are prodrugs. A discussion of prodrugs is provided in (a) Stella, V. J.; Borchardt, R. T.; Hageman, M. J.; Oliyai, R.; Mag, H. et al. *Prodrugs: Challenges and Rewards Part* 1 and Part 2; Springer, p. 726: New York, NY, USA, 2007, (b) Rautio, Kutnpulainen, Heimbach, T,; Oliyai, R.; Oh, D. et al. Prodrugs: design and clinical applications. *Nat. Rev. Drug Discov.* 2008, 7, 255, (c) T. Higuchi and V. Stella, *Pro-drugs as Novel Delivery Systems* (1987) 14 of the A.C.S. Symposium Series, and in (d) *Bioreversible Carriers in Drug Design,* (1987) Edward B. Roche, ed., American Pharmaceutical Association and Pergamon Press. More specifically, compounds of Formula I (or any embodiment thereof and pharmaceutically acceptable salts thereof) are prodrug modifications of tenofovir, which is a mono-phosphonate. The compounds of Formula I may be converted intracellularly (in vivo or in vitro) to the corresponding monophosphate or diphosphate of tenofovir. The conversion may occur by one or more mechanisms, e.g., an enzyme-catalyzed chemical reaction, a metabolic chemical reaction, and/or a spontaneous chemical reaction (e.g., solvolysis), such as, for example, through hydrolysis in blood. While not wishing to be bound by any particular theory, tenofovir diphosphate is generally understood to be responsible for inhibiting the HIV RT enzyme and for the resulting antiviral activity after administration of the compound of Formula I to a subject, Another embodiment of the present invention is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. % or from about 98 wt. % to 100 wt. %), and most preferably at least about 99 wt. % (e.g. 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of Formula I which has one or more asymmetric centers and can occur as mixtures of stereoisomers, a substantially pure compound can be either a substantially pure mixture of the stereoisomers or a substantially pure individual stereoisomer, The compounds of Formula I herein, and pharmaceutically acceptable salts thereof, are useful for HIV reverse transcriptase inhibition and for inhibiting HIV replication in vitro and in vivo. More particularly, the compounds of Formula I for inhibiting the polymerase function of HIV-1 reverse transcriptase. The testing of compounds of the Examples of this invention in the Viking assay set forth in Example 29 below, illustrate the ability of compounds of the invention to inhibit the RNA-dependent DNA polymerase activity of HIV-1 reverse transcriptase. The compounds of Formula I may also be useful agents against HIV-2. The compounds of Examples 1-28 (inclusive of A and B isomers) of the present invention also exhibit activity against drug resistant forms of HIV (e.g., NNRTI-associated mutant strains K103N and/or Y181C; NRTI-associated mutant strains M184V and M184I mutants).

This invention also encompasses methods for the treatment or prophylaxis of infection by HIV, for the inhibition of HIV reverse transcriptase, for the treatment, prophylaxis, or delay in the onset of AIDS in a subject in need thereof, which comprise administering to the subject an effective amount of a compound of the invention or a pharmaceutically acceptable salt thereof.

The invention further encompasses methods for the treatment or prophylaxis of infection by HIV, for the inhibition of HIV reverse transcriptase, for the treatment, prophylaxis, or delay in the onset of AIDS in a subject in need thereof, which comprise administering to the subject an effective amount of a compound of the invention or a pharmaceutically acceptable salt thereof in combination with an effective amount of one or more additional anti-HIV agents selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and. HIV maturation inhibitors.

The invention encompasses a pharmaceutical composition comprising an effective amount of a compound of the invention, or a pharmaceutically acceptable salt thereof, and a pharmaceutically acceptable carrier, The invention also encompasses a pharmaceutical composition comprising an effective amount of a compound of the invention, or a pharmaceutically acceptable salt thereof, and a pharmaceutically acceptable carrier further comprising an effective amount of one or more additional anti-HIV agents selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

The compounds of this invention could also be useful for inhibition of hepatitis B virus (HBV) reverse transcriptase. Accordingly, this invention also encompasses methods for the treatment of chronic hepatitis B infection which comprise administering to the subject an effective amount of a compound of the invention or a pharmaceutically acceptable salt thereof The invention also encompasses a compound of the invention, or a pharmaceutically acceptable salt thereof, for use in the preparation of a medicament for the treatment or prophylaxis of infection by HIV, for the inhibition of HIV reverse transcriptase, or for the treatment, prophylaxis, or delay in the onset of AIDS in a subject in need thereof Other embodiments of the present invention include the following:

(a) A pharmaceutical composition comprising an effective amount of a compound of Formula I or a pharmaceutically acceptable salt thereof, and a pharmaceutically acceptable carrier. In particular embodiments, the pharmaceutical composition comprises a therapeutically effective amount of a compound of Formula I or a pharmaceutically acceptable salt thereof, and a pharmaceutically acceptable carrier. In other embodiments, the pharmaceutical composition comprises a prophylactically effective amount of a compound of Formula I or a pharmaceutically acceptable salt thereof, and a pharmaceutically acceptable carrier.

(b) A pharmaceutical composition which comprises the product prepared by combining (e.g., mixing) an effective amount of a compound of Formula I or a pharmaceutically acceptable salt thereof, and a pharmaceutically acceptable carrier.

(c) The pharmaceutical composition of (a) or (b), further comprising an effective amount of one or more an anti-HIV agents selected from the group consisting of HIV antiviral agents, immunomodulators, and anti-infective agents.

(d) The pharmaceutical composition of (c), wherein the anti-HIV agent is selected from one or more of an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors. HIV entry inhibitors and HIV maturation inhibitors.

(e) A combination which is (i) a compound of Formula I or a pharmaceutically acceptable salt thereof and (ii) an anti-HIV agent selected from the group consisting of HIV antiviral agents, immunomodulators, and anti-infective agents; wherein the compound and the anti-HIV agent are each employed in an amount that renders the combination effective for inhibition of HIV reverse transcriptase, for treatment or prophylaxis of infection by HIV, or for treatment, prophylaxis of or delay in the onset or progression of AIDS.

(f) The combination of (e), wherein the anti-HIV agent is an antiviral selected from the group consisting of HIV protease inhibitors. nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(g) A method for the inhibition of HIV reverse transcriptase in a subject in need thereof which comprises administering to the subject an effective amount of a compound of Formula I or pharmaceutically acceptable salt thereof. In specific embodiments, the method comprises administering to the subject a therapeutically effective amount of a compound of Formula I or a pharmaceutically acceptable salt thereof. In other embodiments, the method comprises administering to the subject a prophylactically effective amount of a compound of Formula I or a pharmaceutically acceptable salt thereof.

(h) A method for the prophylaxis or treatment of infection by HIV (e.g., HIV-1) in a subject in need thereof which comprises administering to the subject an effective amount of a compound of Formula I or pharmaceutically acceptable salt thereof. In specific embodiments, the method comprises administering to the subject a therapeutically effective amount of a compound of Formula I or a pharmaceutically acceptable salt thereof. In other embodiments, the method comprises administering to the subject a prophylactically effective amount of a compound of Formula I or a pharmaceutically acceptable salt thereof.

(i) The method of (h), wherein the compound of Formula I or a pharmaceutically acceptable salt thereof is administered in combination with an effective amount of at least one other HIV antiviral selected from the group consisting of RN protease inhibitors, integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(j) A method for the prophylaxis, treatment or delay in the onset or progression of AIDS in a subject in need thereof which comprises administering to the subject an effective amount of a compound of Formula I or pharmaceutically acceptable salt thereof. In specific embodiments, the method comprises administering to the subject a therapeutically effective amount of a compound of Formula I or a pharmaceutically acceptable salt thereof. In other embodiments, the method comprises administering to the subject a prophylactically effective amount of a compound of Formula I or a pharmaceutically acceptable salt thereof (k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof, which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I or pharmaceutically acceptable salt thereof (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators, Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, aspects, classes, sub-classes, or features described above. In all of these embodiments etc., the compound may optionally be used in the form of a pharmaceutically acceptable salt.

Additional embodiments of the present invention include each of the compounds, pharmaceutical compositions, combinations, methods and uses set forth in the preceding paragraphs, wherein the compound or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula. I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors, HIV-1 entry inhibitors and HIV-1 maturation inhibitors. The compounds of Formula I may also be useful agents against HIV-2.

The term "administration" and variants thereof (e.g., "administering" a compound) in reference to a compound of Formula I means providing the compound to the individual in need of treatment or prophylaxis and includes both self-administration and administration to the patient by another person. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

The term "subject" or "patient" as used herein refers to an animal, preferably a mammal, most preferably a human, who has been the object of treatment, observation or experiment.

The term "effective amount" as used herein means an amount of a compound sufficient to inhibit HIV reverse transcriptase, inhibit HIV replication, exert a prophylactic effect, and/or a exert a therapeutic effect after administration. One embodiment of "effective amount" is a "therapeutically effective amount" which is an amount of a compound that is effective for inhibiting HIV reverse transcriptase, inhibiting HIV replication (either of the foregoing which may also be referred to herein as an "inhibition effective amount"), treating HIV infection, treating AIDS, delaying the onset of AIDS, and/or slowing progression of ARC or AIDS in a patient infected with HIV. Another embodiment of "effective amount" is a "prophylactically effective amount" which is an amount of the compound that is effective for prophylaxis of HIV infection in a subject not infected with HIV or prophylaxis of ARC or AIDS in an HIV-infected patient. It is understood that an effective amount can simultaneously be both a therapeutically effective amount, e.g., for treatment of HIV infection, and a prophylactically effective amount, e.g., for prevention or reduction of risk for developing AIDS in a subject infected with HIV. The term "preventing," as used herein with respect to an HIV viral infection or AIDS, refers to reducing the likelihood or severity of HIV infection or AIDS. When the compound of Formula I is administered as a salt, reference to an amount of the compound in milligrams or grams is based on the free form (i.e., the non-salt form) of the compound. In the combination therapies of the present invention, an effective amount can refer to each individual agent or to the combination as a whole, wherein the amounts of all agents administered in the combination are together effective, but wherein a component agent of the combination may or may not be present individually in an effective amount with reference to what is considered effective for that component agent if it were administered alone.

In the method of the present invention (i.e., inhibiting HIV reverse transcriptase, treating or prophylaxis of HIV infection, inhibiting HIV replication, treating or prophylaxis of AIDS, delaying the onset of AIDS, or delaying or slowing progression of AIDS), the compounds of this invention, optionally in the form of a. salt, can be administered by means that produce contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally (e.g., via tablet or capsule), parenterally (including subcutaneous injections, intravenous, intramuscular or intrasternal injection, or infusion techniques), by inhalation spray, or rectally, in the form of a unit dosage of a pharmaceutical composition containing an effective amount of the compound and conventional non-toxic pharmaceutically acceptable carriers, adjuvants and vehicles. The compound could also be administered via an implantable drug delivery device adapted to provide an effective amount of the compound or a pharmaceutical composition of the compound over an extended period of time, for example but not limited to, over the course of a month, 3 months, 6 months or a year.

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Implantable compositions can be prepared according to methods known in the art wherein the carrier comprises the active chemical ingredient with polymers as suitable excipients, or utilizing an implantable device for drug delivery. Further description of methods suitable for use in preparing pharmaceutical compositions for use in the present invention and of ingredients suitable for use in said compositions is provided in Remington's Pharmaceutical Sciences, $18^{th}$ edition, edited by A. R. Gennaro, Mack Publishing Co., 1990 and in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Formulations of compounds described by Formula. I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are known in the art. For example, solid dispersions can be prepared using excipients and processes as described in reviews (e.g., A.T.M. Serajuddin, J Pharm Sci, 88:10, pp. 1058-1066 (1999)). Nanoparticulate systems based on both attrition and direct synthesis have also been described in reviews such as Wu et al (F. Kesiso$_L$tiou, S. Panmai, Y. Wu, Advanced Drug Delivery Reviews, 59:7 pp. 631-644 (2007)).

The compounds of Formula I can be administered in a dosage range of 0.001 to 1000 mg/kg of mammal (e.g., human) body weight per day, or at longer time intervals on non-consecutive days as appropriate, in a single dose or in divided doses. One example of a dosage range is 0.01 to 500 mg/kg body weight per day, or at other time intervals as appropriate, administered orally or via other routes of administration in a single dose or in divided doses. Another example of a dosage range is 0.1 to 100 mg/kg body weight per day, or at other time intervals as appropriate, administered orally or via other routes of administration in single or divided doses. Another example of a dosage range is 50 mg to 1 gram per day, in a single dose or divided doses.

Daily or weekly administration or less frequent dosing regimens with longer time intervals on non-consecutive days (as discussed below), can be via any suitable route of administration, e.g., but not limited to, oral or parenteral. Daily or weekly administration is preferably via oral administration. For either a daily or weekly dosing regimen, on each day (calendar day or about a 24 hour period of time) of drug administration (the "administration day"), the desired dosage amount may be administered once per administration day or in divided dosage amounts administered at two or more staggered times during the administration day, e.g., a first administration followed about 12 hours later with a second administration during the course of an administration day (the "dosage times)"). The desired dosage amount at each of the one or more dosage times on an administration day can be administered via one oral dosage unit such as a tablet, or more than one oral dosage unit as appropriate. Preferably the administration is via a single oral dosage unit, e.g, a tablet, once per administration day.

For weekly or less frequent dosing regimens with longer time intervals on non-consecutive days, a parenteral route of administration may be employed. Examples of dosing regimens with longer time intervals on non-consecutive days include but are not limited to administration weekly (every seventh day with leeway as to exact date of dosing), bi-weekly (every two weeks with leeway as to exact date of dosing), monthly (e.g., every 30 days, or the same calendar day each month with leeway as to exact date of dosing), bimonthly (e.g., every 60 days, or the same calendar day every two months with leeway as to exact date of dosing), every 3 months (e.g., every 90 days, or the same calendar day every three months with leeway as to exact date of dosing), every six months (e.g., every 180 days, or the same calendar day every six months with leeway as to exact date of dosing), or yearly (e.g., every 12 months with leeway as to exact date of the annual dosing). "Leeway" is intended to mean that the dosing regimens described herein also encompasses those wherein the patient generally follows the time intervals between administration days including when the interval is not always strictly followed by the patient, e.g., a weekly dosing regimen where the patient may take the drug product the day before or the day after the seventh day following the prior administration day for one or more weeks. The leeway time may increase as the dosing regimen interval increases. For oral (e.g., tablets or capsules) or other routes of administration, the dosage units may contain 1.0 mg to 1000 mg of the active ingredient, for example but not limited to, 1, 5, 10, 15, 20, 25, 50, 75, 100, 150, 200, 250, 300, 350, 400, 450, 500, 600, 700, 800, 900 or 1000 milligrams of the active ingredient for the symptomatic adjustment of the dosage to the patient to be treated. Furthermore, the compound may be formulated in oral formulations for immediate or modified release such as extended or controlled release.

The favorable pharmacokinetic profile of tested compounds of this invention may also render the compounds suitable for less frequent dosing. Thus, the compounds of the invention could be administered orally, weekly or parenterally at longer time intervals as described above, For parenteral administration, the compositions can be administered, e.g., intravenously (IV) or intramuscularly (IM) via injection, or using other infusion techniques. One or more of such injections or infusions may be administered at each dosing time interval as needed to deliver the appropriate amount of active agent. The compound could also be administered subcutaneously using an implantable device. For parenteral administration including implantable devices employing longer duration dosing intervals such as monthly, every 3 months, every 6 months, yearly or longer intervals, the dosage amount would be adjusted upward as needed to provide effective treatment during the time intervals between administration of each dose.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In sonic cases, depending on the potency of the compound or the individual response, it may be necessary to deviate upwards or downwards from the given dose. The amount and frequency of administration will be regulated according to the judgment of the attending clinician considering such factors.

As noted above, the present invention is also directed to use of a compound of Formula I with one or more anti-HIV agents. An "anti-HIV agent" is any agent which is directly or indirectly effective in the inhibition of HIV, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows, or a pharmaceutically acceptable salt thereof:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRT1 |
| dolutegravir, Tivicay ® | InI |
| doravirine, MK-1439 | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| Rilpivirine | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tipranavir, Aptivus ® | PI |
| vicriviroc | EI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, 57$^{th}$ edition (2003), the 58$^{th}$ edition (2004), or the 59$^{th}$ edition (2005) and the Physicians' Desk Reference (68$^{th}$ ed.). (2014), Montvale, N.J.: PDR Network. The dosage ranges for a compound of the invention in these combinations can be the same as those set forth above.

The compounds of this invention are also useful in the preparation and execution of screening assays for antiviral compounds. For example, the compounds of this invention can be useful for isolating enzyme mutants, which are excellent screening tools for more powerful antiviral compounds. Furthermore, the compounds of this invention can be useful in establishing or determining the binding site of other antivirals to HIV reverse transcriptase, e.g., by competitive inhibition.

Abbreviations and acronyms employed herein include the following:

| | |
|---|---|
| Ac | acetyl |
| ACN | acetonitrile |
| AcOH or HOAc | acetic acid |
| APCI | atmospheric-pressure chemical ionization |
| Aq | aqueous |
| amu | atomic mass units |
| Bn | benzyl |
| Boc or BOC | tert-butoxycarbonyl |
| Bu | butyl |
| Bz | benzoyl |
| calc'd | calculated |
| cBu | cyclobutyl |
| Cbz | benzyloxycarbonyl |
| cHex | cyclohexyl |
| cPen | cyclopentyl |
| cPr | cyclopropyl |
| DBU | 1,8-diazabicycloundec-7-ene |
| DCE | 1,2-dichloroethane |
| DCM | dichloromethane |
| DIEA or Hünig's base | N,N-diisopropylethylamine |
| DMA | 1,2-dimethylacetamide |
| DMF | dimethylformamide |
| DMSO | dimethyl sulfoxide |
| EDC | 1-ethyl-3-(3-dimethylaminopropyl)carbodiimide |
| EDTA | ethylenediamine tetraacetic acid |
| ESI | electrospray ionization |
| Et | ethyl |
| EtOH | ethanol |
| EtOAc | ethyl acetate |
| G | grams |
| H | hour |
| HATU | N,N,N',N',-tetramethyl-O-(7-azabenzotriazol-1-yl)uronium hexafluorophosphate |
| HOBt | 1-hydroxybenzotriazole |
| HPLC | high-performance liquid chromatography |
| IPA | isopropanol |
| iPr | isopropyl |
| LC | liquid chromatography |
| LCMS | liquid chromatography mass spectrometry |
| mCPBA | m-choroperoxybenzoic acid |
| Me | Methyl |
| MeOH | methanol |
| mg | milligrams |
| min | Minute |
| μL | microliters |
| mL | milliliters |
| mm | millimeter |
| mmol | millimoles |
| μM | micromolar |
| MS | mass spectrometry |
| Ms | methanesulfonyl (mesyl) |
| MTBE | methyl tert-butyl ether |
| nm | nanometer |
| nM | nanomolar |
| NMR | nuclear magnetic resonance spectroscopy |
| obsv'd | observed |
| Ph | Phenyl |
| Pr | Propyl |
| rac | racemic mixture |
| RT or rt | room temperature (ambient, about 25° C.) |
| sat or sat'd. | saturated |
| SFC | supercritical fluid chromatography |
| tBu | tert-butyl |

-continued

| | |
|---|---|
| TEA | triethylamine ($Et_3N$) |
| TFA | trifluoroacetic acid |
| THF | tetrahydrofuran |
| TLC | thin layer chromatography |

Methods for preparing the exemplified compounds of this invention are described in the following Scheme and Examples. Starting materials and intermediates were purchased commercially from common catalog sources or were made using known procedures, or as otherwise illustrated. In some cases the order of carrying out the reaction steps in the schemes may be varied to facilitate the reaction or to avoid unwanted reaction products.

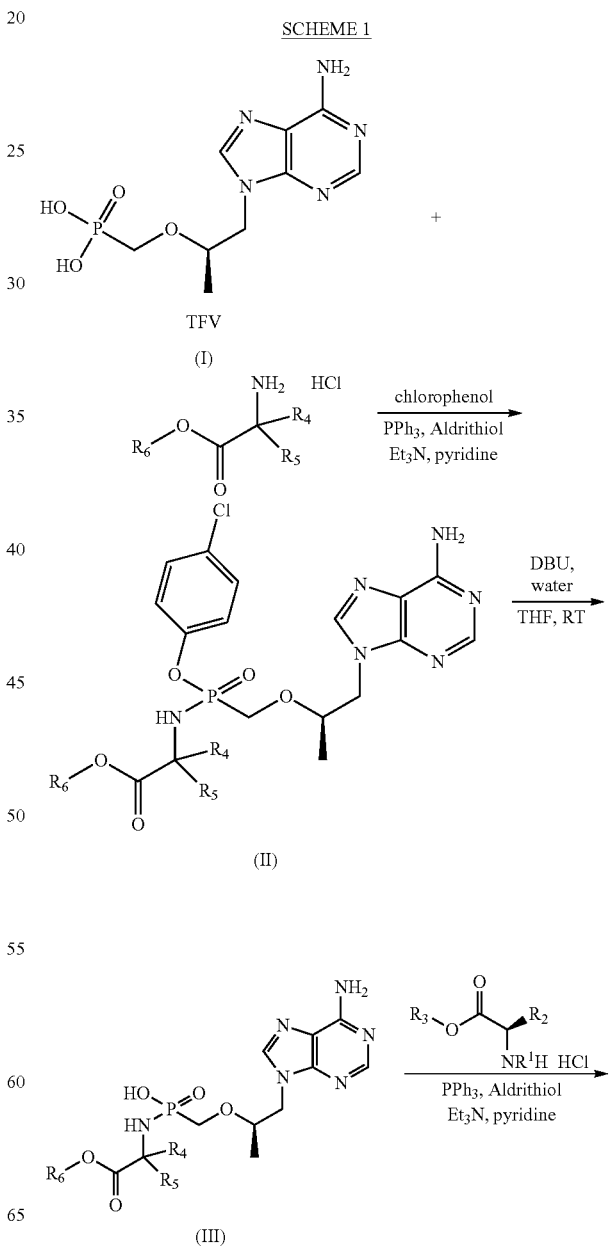

SCHEME 1

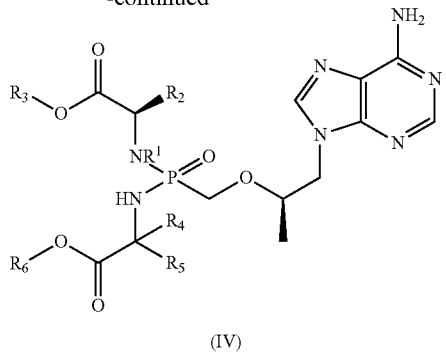

(IV)

Compounds of Formula IV can be prepared from (R)-(((1-(6-amino-9H-purin-9-yl)propan-2-yl)oxy)methyl)phosphonic acid (I, referred to herein as TFV) though a three-step sequence. First, TFV can undergo functionalization with variably-substituted unnatural geminal amino esters and chlorophenol in a one-step one-pot condensation reaction with 2,2'-dipyridyldisulfide (Aldrithiol), triphenylphosphine, and base to provide intermediates of Formula II. This intermediate is then hydrolyzed in the presence of base and water to provide intermediates of Formula III, which are unstable and are used immediately in the subsequent coupling reaction. Intermediates of Formula III can then undergo functionalization with variably-substituted unnatural D-amino esters by a condensation reaction with 2,2'-dipyridyldisulfide (Aldrithiol), triphenylphosphine, and base to provide intermediates of the current invention (Formula IV). Amino esters that are not commercially available can be readily prepared by condensation between the corresponding amino acid and alcohols with thionyl chloride.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50mm, 5 µm or a Waters Acquity UPLC® BEH C18 1.0×50 mm, 1.7 µm. The flow rate was 1 mL/min, and the injection volume was 10 µL. UV detection was in the range 210-400 nm. The mobile phase consisted of solvent A (water plus 0.05% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 mm.

Preparative HPLC purifications were usually performed using either a mass spectrometry directed system or a non-mass spectrometry guided system. Usually they were performed on a Waters Chromatography Workstation configured with a LC-MS System consisting of: Waters ZQ™ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TEA. Flow rates were maintained at 50 mL/min, the injection volume was 1800 µL, and the UV detection range was 210-400 nm. An alternate preparative HPLC system used was a Gilson Workstation consisting of: Gilson GX-281 Injector/Collector, Gilson UV/VIS-155 Detector, Gilson 333 and 334 Pumps, and either a Phenomenex Gemini-NX C-18 5 micron, 50 mm (id) x 250 mm column or a Waters XBridge™ C-18 5 micron OBD™, 30 mm (id)×250 mm column. The mobile phases consisted of mixtures of acetonitrile (0-75%) in water containing 5mmol (NH$_4$)HCO$_3$. Flow rates were maintained at 50 mL/min for the Waters Xbridge™ column and 90 mL/min for the Phenomenex Gemini column. The injection volume ranged from 1000-8000 µL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO Combi-Flash® Companion XL on silica gel (32-63 µM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as an internal reference in CD$_3$Cl solutions, and residual CH$_3$OH peak or TMS was used as an internal reference in CD$_3$OD solutions. Coupling constants (J) were reported in hertz (Hz). Chiral analytical chromatography was most commonly performed on one of CHIRALPAK® AS, CHIRALPAK® AD, CHIRALCEL® OD, CHIRALCEL® IA, or CHIRALCEL® OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of CHIRALPAK AS, CHIRALPAK AD, CHIRALCEL® OD, CHIRALCEL®IA, CHIRALCEL® OJ columns (20×250 mm) (Daicel Chemical Industries, Ltd.) with desired isocratic solvent systems identified on chiral analytical chromatography or by supercritical fluid (SFC) conditions.

Several methods for preparing the compounds of this invention are also described in the Examples. Starting materials and intermediates were purchased commercially from common catalog sources or were made using known procedures, or as otherwise illustrated. Some frequently applied routes to the compounds of Formula I are also described by the schemes as illustrated in the following examples. In some cases the order of carrying out the steps of reaction schemes may be varied to facilitate the reaction or to avoid unwanted reaction products.

It is understood that a chiral center in a compound may exist in the "S" or "R" stereoconfigurations, or as a mixture of both, unless specifically noted otherwise. In some of the following examples, compounds having a chiral center were separated into single stereoisomers, referred to as Isomer A (faster eluting isomer) and Isomer B (slower eluting isomer), based on their observed elution order resulting from the separation as performed. Except for the defined chiral centers in the parent stereoisomer mixture, absolute stereochemistry (R or S) of each of the separated stereoisomers was not determined, unless specifically noted otherwise. In examples where absolute stereochemistry of each of the separated isomers was not determined, an asterisk (*) may be used in the associated chemical structure drawing that indicates the location of the unassigned chiral center.

INTERMEDIATE A

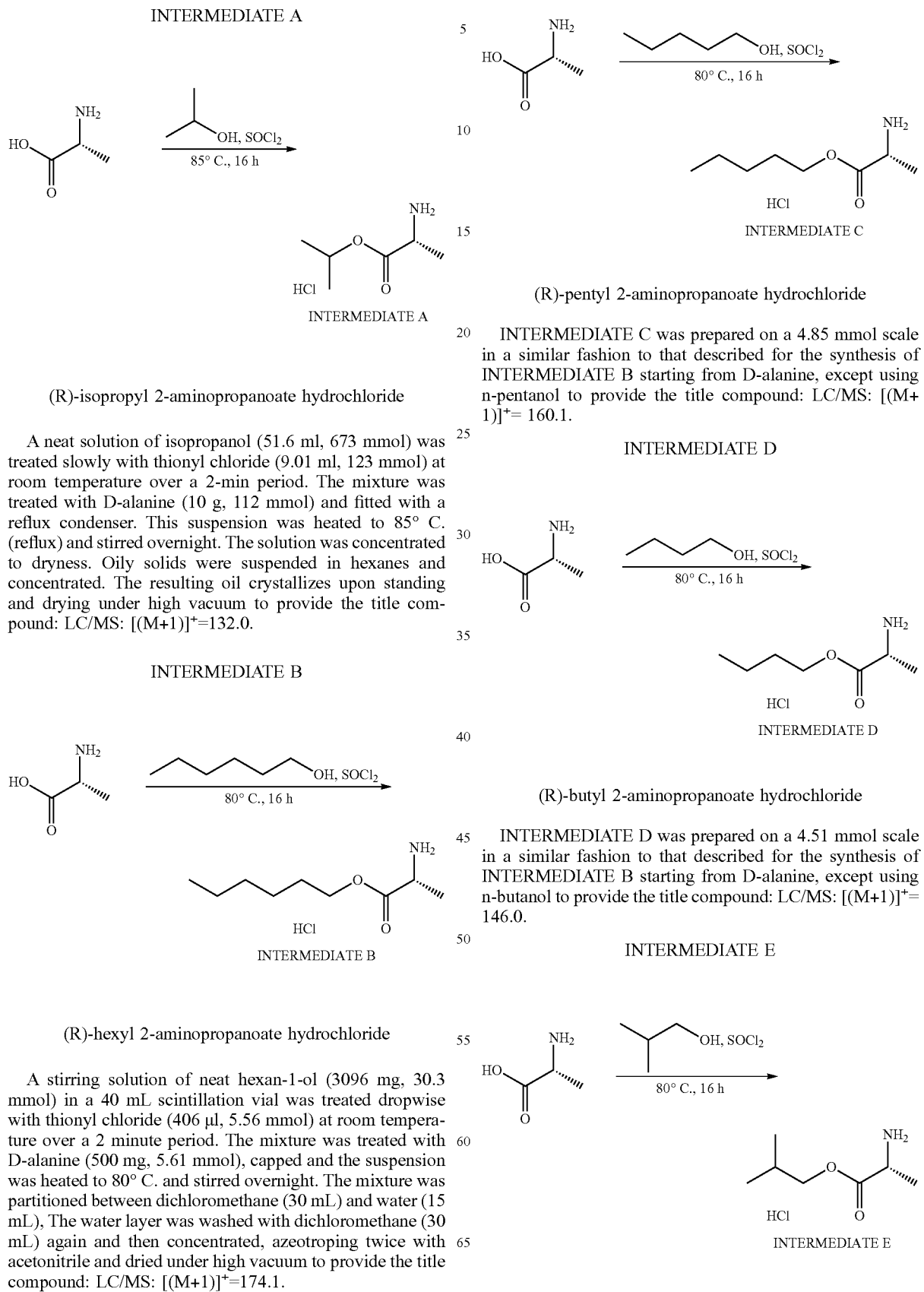

(R)-isopropyl 2-aminopropanoate hydrochloride

A neat solution of isopropanol (51.6 ml, 673 mmol) was treated slowly with thionyl chloride (9.01 ml, 123 mmol) at room temperature over a 2-min period. The mixture was treated with D-alanine (10 g, 112 mmol) and fitted with a reflux condenser. This suspension was heated to 85° C. (reflux) and stirred overnight. The solution was concentrated to dryness. Oily solids were suspended in hexanes and concentrated. The resulting oil crystallizes upon standing and drying under high vacuum to provide the title compound: LC/MS: [(M+1)]$^+$=132.0.

INTERMEDIATE B (R)-hexyl 2-aminopropanoate hydrochloride

A stirring solution of neat hexan-1-ol (3096 mg, 30.3 mmol) in a 40 mL scintillation vial was treated dropwise with thionyl chloride (406 µl, 5.56 mmol) at room temperature over a 2 minute period. The mixture was treated with D-alanine (500 mg, 5.61 mmol), capped and the suspension was heated to 80° C. and stirred overnight. The mixture was partitioned between dichloromethane (30 mL) and water (15 mL), The water layer was washed with dichloromethane (30 mL) again and then concentrated, azeotroping twice with acetonitrile and dried under high vacuum to provide the title compound: LC/MS: [(M+1)]$^+$=174.1.

INTERMEDIATE C (R)-pentyl 2-aminopropanoate hydrochloride

INTERMEDIATE C was prepared on a 4.85 mmol scale in a similar fashion to that described for the synthesis of INTERMEDIATE B starting from D-alanine, except using n-pentanol to provide the title compound: LC/MS: [(M+1)]$^+$= 160.1.

INTERMEDIATE D (R)-butyl 2-aminopropanoate hydrochloride

INTERMEDIATE D was prepared on a 4.51 mmol scale in a similar fashion to that described for the synthesis of INTERMEDIATE B starting from D-alanine, except using n-butanol to provide the title compound: LC/MS: [(M+1)]$^+$= 146.0.

INTERMEDIATE E

(R)-isobutyl 2-aminopropanoate hydrochloride

INTERMEDIATE E was prepared on a 3.37 mmol scale in a similar fashion to that described for the synthesis of INTERMEDIATE B starting from D-alanine, except using isobutanol to provide the title compound: LC/MS: [(M+1)]$^+$= 146.0.

INTERMEDIATE F

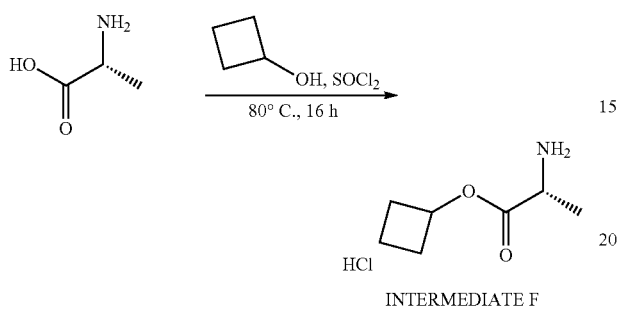

INTERMEDIATE F

(R)-cyclobutyl 2-aminopropanoate hydrochloride

INTERMEDIATE F was prepared on a 14.5 mmol scale in a similar fashion to that described for the synthesis of INTERMEDIATE A starting from D-alanine, except using cyclobutanol to provide the title compound: LC/MS: [(M+1)]$^+$=144.0.

INTERMEDIATE G

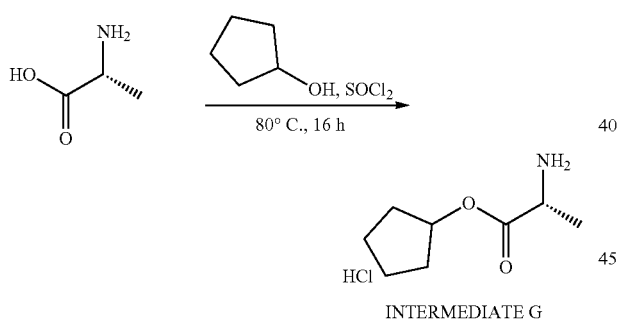

INTERMEDIATE G

(R)-cyclopentyl 2-aminonropanoate hydrochloride

INTERMEDIATE G was prepared on a 80 mmol scale in a similar fashion to that described for the synthesis of INTERMEDIATE G starting from D-alanine, except using cyclopentanol to provide the title compound: LC/MS: [(M+1)]$^+$=158.0.

INTERMEDIATE H

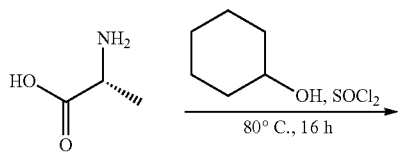

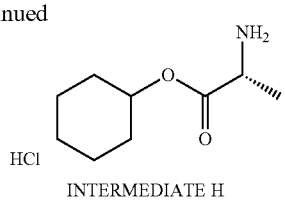

INTERMEDIATE H

(R)-cyclohexyl 2-aminopropanoate hydrochloride

INTERMEDIATE H was prepared on a 4 mmol scale in a similar fashion to that described for the synthesis of INTERMEDIATE B starting from D-alanine, except using cyclohexanol to provide the title compound: LC/MS: [(M+1)]$^+$=172.1.

INTERMEDIATE I

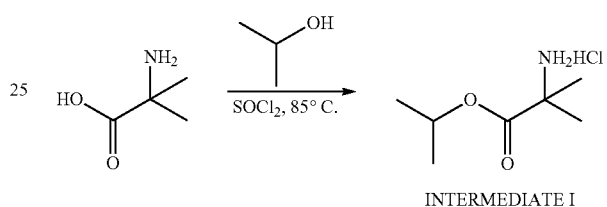

INTERMEDIATE I isopropyl 2-amino-2-methylpropanoate hydrochloride

A neat solution of isopropanol (89 ml, 1164 mmol) was treated slowly with thionyl chloride (15.57 ml, 213 mmol) at room temperature over a 2 min period. The mixture was treated with 2-amino-2-methylpropanoic acid (20 g, 194 mmol) and fitted with a reflux condenser. This suspension was heated to 85° C. (reflux) and stirred for 3 days. The resulting clear solution was concentrated to dryness. The resulting oil was crystallized by trituration in diethyl ether and hexanes. The solids were isolated by filtration and dried under high vacuum to provide the title compound: LC/MS: [(M+1)]$^+$=146.1.

INTERMEDIATE J

INTERMEDIATE J butyl 2-amino-2-methylpropanoate hydrochloride

INTERMEDIATE J was prepared on a 8 mmol scale in a similar fashion to that described for the synthesis of INTER- MEDIATE I starting from 2-amino-2-methylpropanoic acid, except using n-butanol to provide the title compound: LC/MS: [(M+1)]⁺=160.1.

INTERMEDIATE K

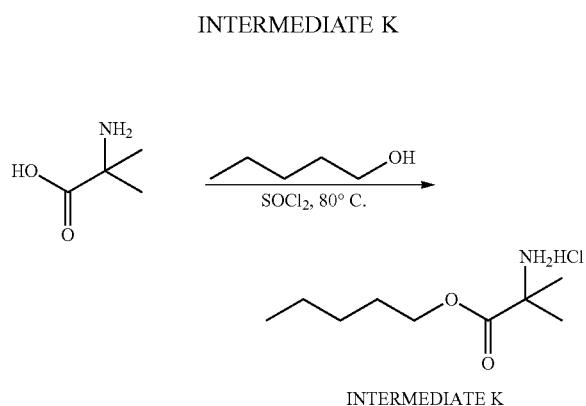

INTERMEDIATE K pentyl 2-amino-2-methylpropanoate hydrochloride

A neat solution of pentan-1-ol (205 g, 2327 mmol) was treated slowly with thionyl chloride (15,57 ml, 213 mmol) at room temperature over a 10 min period (exotherm to ~60° C.). The mixture was treated with 2-amino-2-methylpropanoic acid (40 g, 388 mmol) and fitted with a reflux condenser and stirred at 80° C. over the weekend. The reaction mixture was concentrated under reduced pressure and then dissolved in water (1 L) and washed with 1:1 EtOAc/hexane (2×2 L), hexanes (1×2 L) and dichloromethane (3×1 L). The aqueous layer was concentrated and azeotroped with acetonitrile and then toluene. The residue was dried overnight under high vacuum. The solids were triturated with ~500 mL of diethyl ether, filtered and dried to afford the title compound: LC/MS: [(M+1)]⁺=174.1.

INTERMEDIATE L

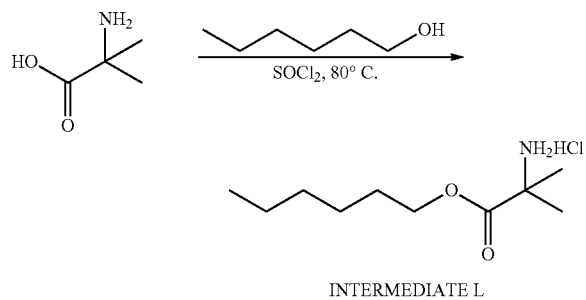

INTERMEDIATE L hexyl 2-amino-2-methylpropanoate hydrochloride

INTERMEDIATE L was prepared on a 388 mmol scale in a similar fashion to that described for the synthesis of INTERMEDIATE K starting from 2-amino-2-methylpropanoic acid, except using n-hexanol to provide the title compound: LC/MS: [(M+1)]⁺=188.1.

INTERMEDIATE M

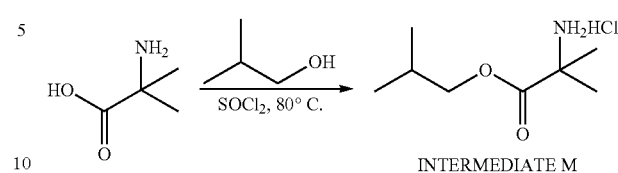

INTERMEDIATE M isobutyl 2-amino-2-methylpropanoate hydrochloride

INTERMEDIATE M was prepared on a 9.15 mmol scale in a similar fashion to that described for the synthesis of INTERMEDIATE K startimg from from 2-amino-2-methylpropanoic acid, except using isobutanol to provide the title compound: LC/MS: [(M+1)]⁺=160.1.

INTERMEDIATE N

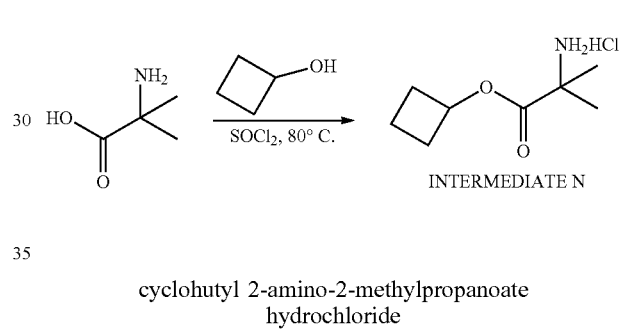

INTERMEDIATE N cyclohutyl 2-amino-2-methylpropanoate hydrochloride

INTERMEDIATE N was prepared on a 11.62 mmol scale in a similar fashion to that described for the synthesis of INTERMEDIATE K starting from from 2-amino-2-methylpropanoic acid, except using cyclobutanol to provide the title compound: LC/MS: [(M+1)]⁺=158.0.

INTERMEDIATE O

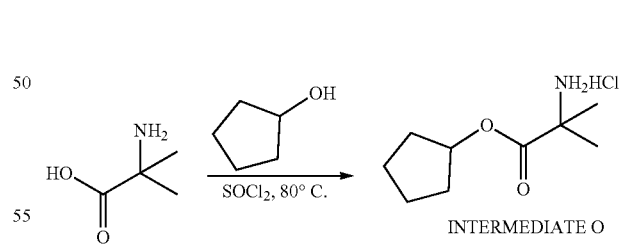

INTERMEDIATE O cyclopentYl 2-amino-2-methylpropanoate hydrochloride

INTERMEDIATE O was prepared on a 15.84 mmol scale in a similar fashion to that described for the synthesis of INTERMEDIATE K starting from from 2-amino-2-methylpropanoic acid, except using cyclopentanol to provide the title compound: LC/MS: [(M+1)]⁺=172.1.

INTERMEDIATE P

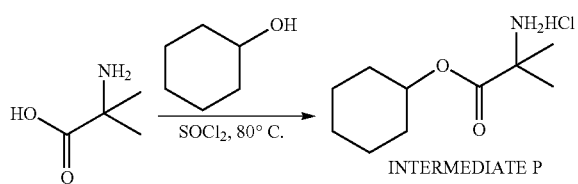

cyclohexyl 2-amino-2-methylproparioate hydrochloride

INTERMEDIATE P was prepared on a 9.2 mmol scale in a similar fashion to that described for the synthesis of INTERMEDIATE K starting from from 2-amino-2-methyl-propanoic acid, except using cyclohexanol to provide the title compound: LC/MS: $[(M+1)]^+=186.1$.

INTERMEDIATE Q

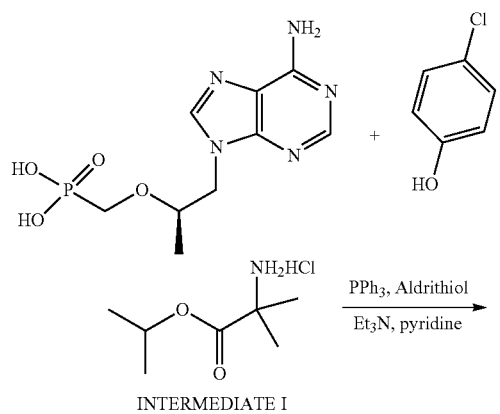

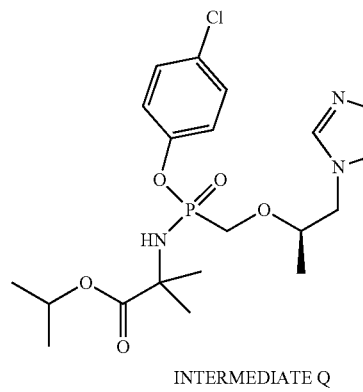

INTERMEDIATE Q isopropyl 2-((((((R)-1-(6-amino-9H-purin-9-yl)propan-2yl)oxy)methyl)(4-chlorophenoxy)-phosphoryl)amino)-2-methylpropanoate A mixture of (R)-(((1-(6-amino-9H-purin-9-yl)propan-2-ypoxy)methyl)phosphonic acid (referred to herein as TFV, 19 g, 66.2 mmol), 4-chlorophenol (6.87 ml, 69.5 mmol), INTERMEDIATE I (12.62 g, 69.5 mmol), and triethylamine (55.3 ml, 397 mmol) in pyridine (221 mL) was heated to 60° C. for 5 minutes with stirring. A freshly prepared solution of 2,2'-dipyridyl disulfide (Aldrithiol, 102 g, 463 mmol) and triphenylphosphine (121 g, 463 mmol) in pyridine (221 mL) was added to the mixture. The reaction was stirred at 60° C. over the weekend. The mixture was cooled to room temperature and concentrated to remove most of the pyridine. The residue was directly purified by gradient elution on silica gel (RediSep-Rf-1.5 kg, 0-10% MeOH/DCM, 1 h gradient) to yield pure fractions which were concentrated to afford the title compound: LC/MS: $[(M+1)]^+=525.2$.

INTERMEDIATE R

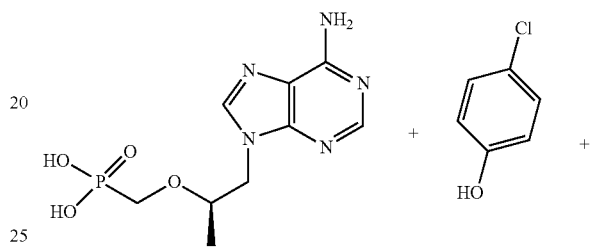

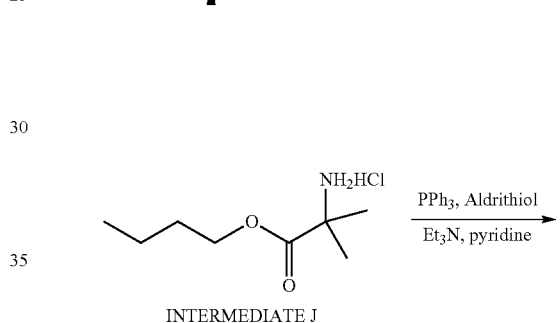

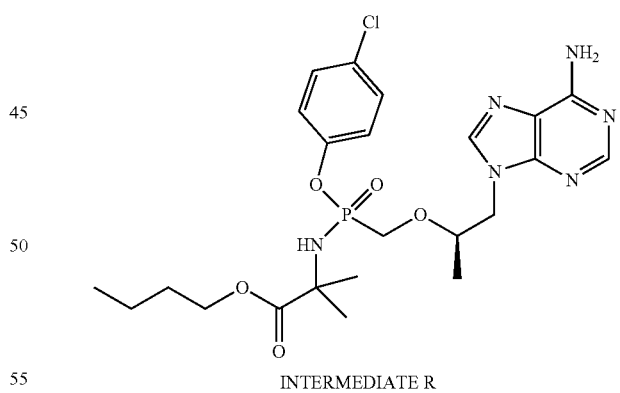

INTERMEDIATE R butyl 2-((((((R)-1-(6-amino-9H-purin9-yl)propan-2-yl)oxy)methyl)(4-chlorophenoxy)phosphoryl)amino)-2-methylpropanoate INTERMEDIATE R was prepared on a 3.13 mmol scale in a similar fashion to that described for the synthesis of INTERMEDIATE Q starting from TFV, chlorophenol, and INTERMEDIATE J: LC/MS: $[(M+1)]^+=539.2$.

INTERMEDIATE S

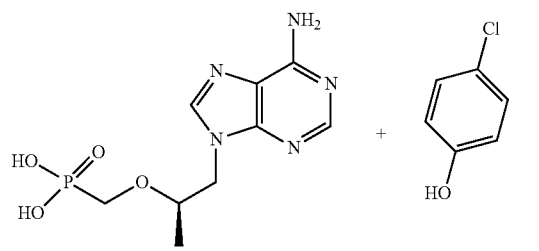

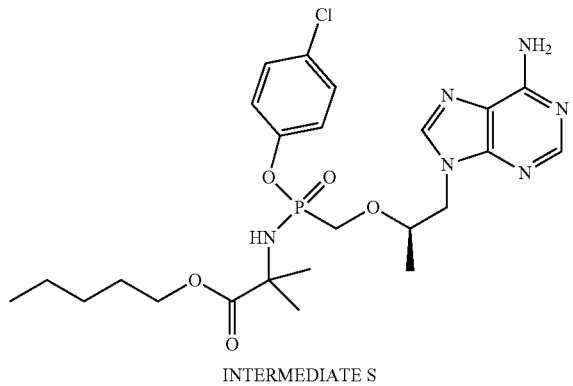

pentyl 2-((((((R)-1-(6-amino-9H-purin-9-yl)propan-2-yl)oxy)methyl)(4-chlorophenoxy)phosphoryl)amino)-2-methylpropanoate INTERMEDIATE S was prepared on a 25.7 mmol scale in a similar fashion to that described for the synthesis of INTERMEDIATE Q starting from TFV, chlorophenol, and INTERMEDIATE K: LC/MS: $[(M+1)]^+=553.2$.

INTERMEDIATE T

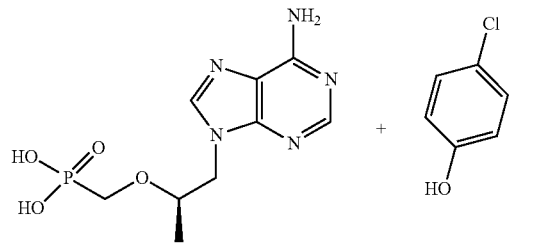

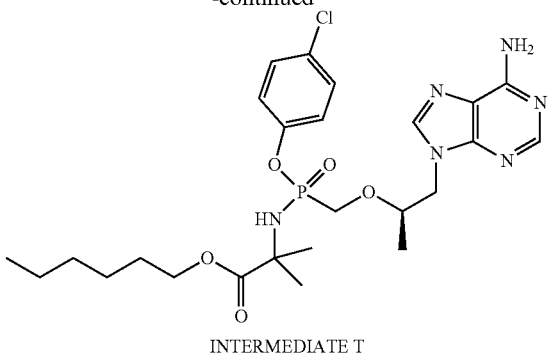

hexyl 2-((((((R)-1-(6-amino-9H-purin-9yl)propan-2-yl)oxy)methyl)(4-chlorophenoxy)phosphoryl)amino)-2-methylpropanoate INTERMEDIATE T was prepared on a 14.25 mmol scale in a similar fashion to that described for the synthesis of INTERMEDIATE Q starting from TFV, chlorophenol, and INTERMEDIATE L: LC/MS: $[(MH+1)]^+=567.3$.

INTERMEDIATE U

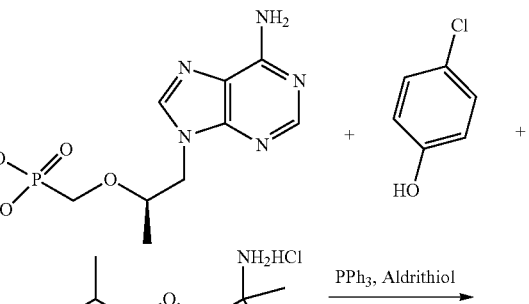

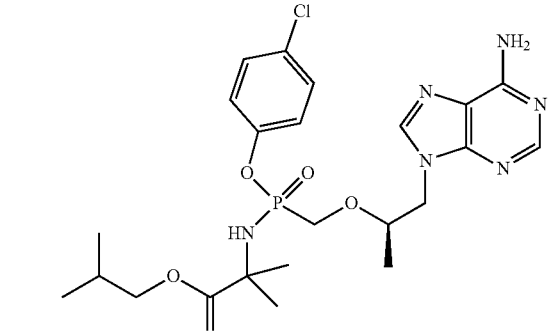

isobutyl 2-((((((R)-1-(6-amino-9H-purin-9-yl)propan-2yl)oxy)methyl)(4-chlorophenoxy)phosphoryl)amino)-2-methylpropanoate INTERMEDIATE U was prepared on a 3.3 mmol scale in a similar fashion to that described for the synthesis of INTERMEDIATE Q starting from TFV, chlorophenol, and INTERMEDIATE M LC/MS: $[(M+1)]^+=539.3$.

INTERMEDIATE V

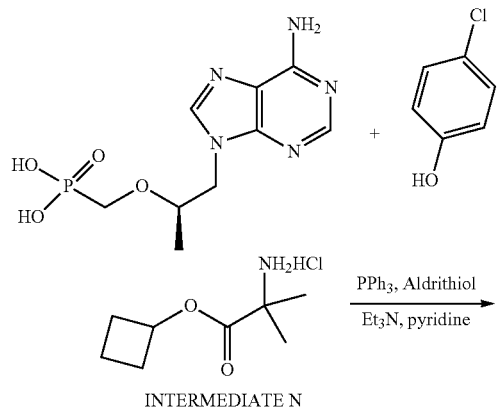

cyclobutyl 2-((((((R)-1-(6-amino-9H-purin-9yl)propan-2-yl)oxy)methyl)(4-chlorophenoxy)phosphoryl)amino)-2-methylpropanopate INTERMEDIATE V was prepared on a 0.42 mmol scale in a similar fashion to that described for the synthesis of INTERMEDIATE Q starting from TFV, chlorophenol, and INTERMEDIATE N: LC/MS: $[(MH+1)]^+=537.2$.

INTERMEDIATE W

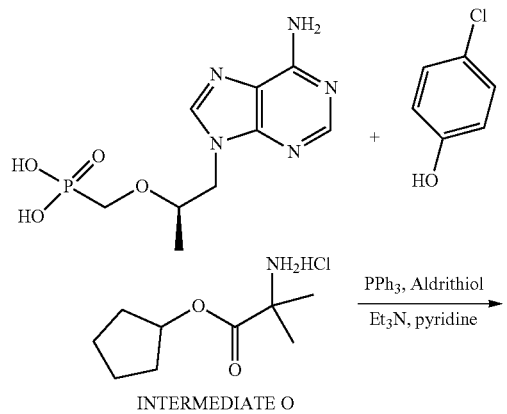

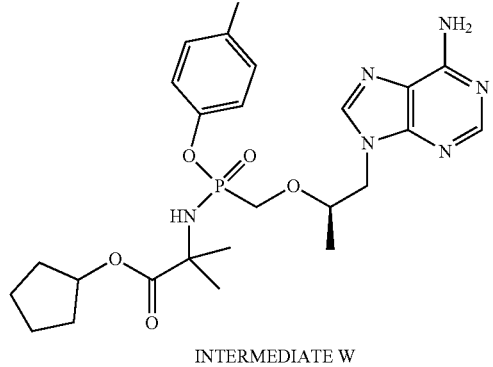

INTERMEDIATE W cyclopentyl 2-((((((R)-1-(6-amino-9H-purin-9-yl)propan-2-yl)oxy)methyl)(4-chlorophenoxy)phosphoryl)amino)-2-methylpropanoate INTERMEDIATE W was prepared chlorophenoxy)nhosnhorvllarnino)-2-methvlnronarioate: INTERMEDIATE W was prepared on a 0.13 mmol scale in a similar fashion to that described for the synthesis of INTERMEDIATE Q starting from TFV, chtorophenol, and INTERMEDIATE O: LC/MS: $[(M+1)]^+=551.2$.

INTERMEDIATE X

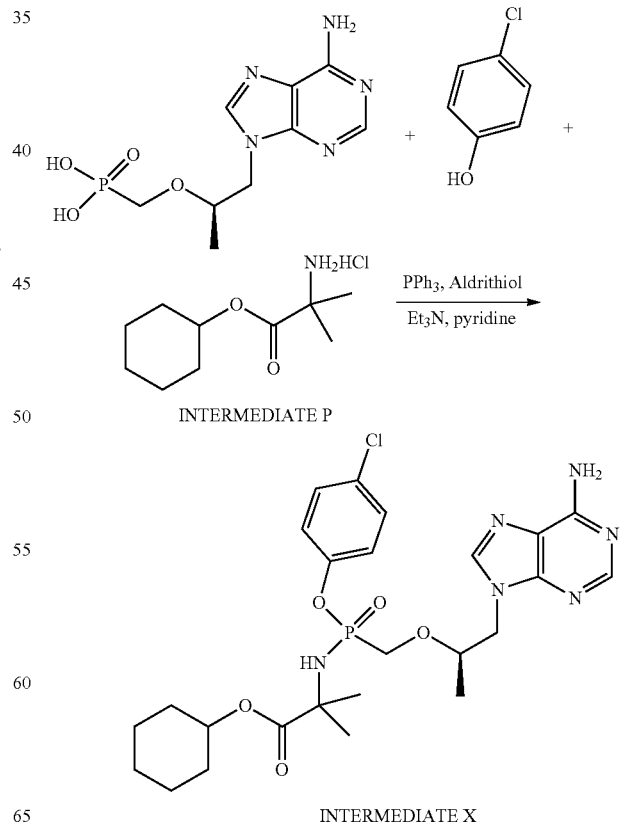

INTERMEDIATE X cyclohexyl 2-((((((R)-1-(6-amino-9H-purin-9-yl)propan-2-yl)oxy)methyl)(4-chlorophenoxy)phosphoryl)amino)-2-methylpropanoate INTERMEDIATE X was prepared on a 0.18 mmol scale in a similar fashion to that described for the synthesis of INTERMEDIATE Q starting from TFV, chlorophenol, and INTERMEDIATE P: LC/MS: [(M+1)]$^+$=565.2.

EXAMPLE 1A/B

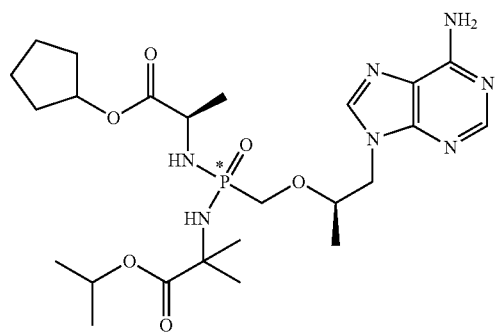

1A/B isopropyl2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate; and
isopropyl2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate

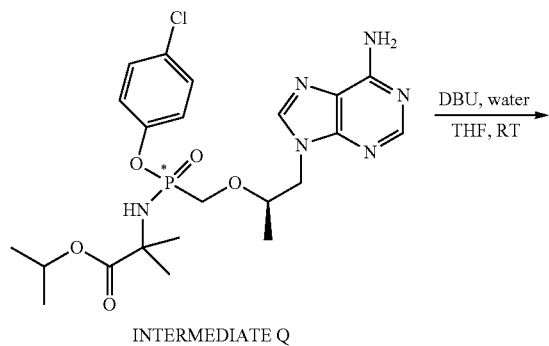

INTERMEDIATE Q

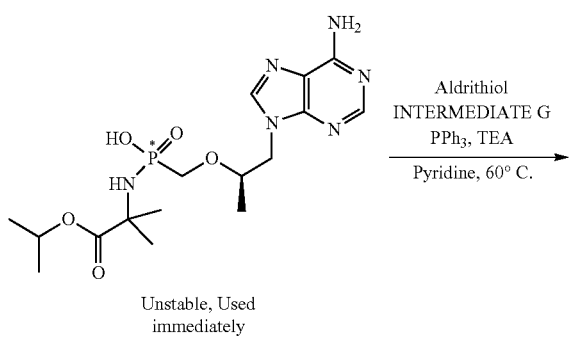

Unstable, Used immediately

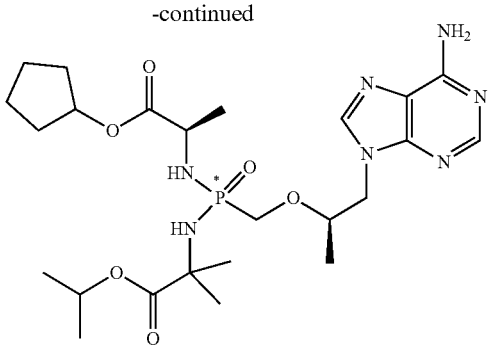

1A/B isopropyl2-((((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate (1A/B):

A mixture of INTERMEDIATE Q (3.8 g, 7.24 mmol) and water (2.61 ml, 145 mmol) in tetrahydrofuran (20 mL) was treated with DBU (1.64 mL, 10.86 mmol) and stirred at room temperature for 2 hr. The mixture was concentrated and the residue was diluted with water (75 mL) and washed with CHCl$_3$ (8×30 mL) to remove the chlorophenol byproduct. The desired product stayed in the aqueous layer. The aqueous layer was concentrated, azeotroping twice with acetonitrile and once with toluene and was dried under high vacuum to afford the unstable intermediate: LC/MS: [(M+1)]$^+$=415.2. This intermediate was used immediately.

A mixture of the above intermediate (3 g, 7.24 mmol), INTERMEDIATE G (1.682 g, 8.69 mmol) and triethylamine (4.04 ml, 29.0 mmol) in pyridine (24 mL) was heated to 60° C. for 5 min. A freshly prepared solution of 2,2'-dipyridyl disulfide (Aldrithiol, 4.78 g, 21.72 mmol) and triphenylphosphine (5.70 g, 21.72 mmol) in pyridine (24 mL) was added to the mixture. The reaction was stirred at 60° C. overnight. The mixture was cooled to room temperature and concentrated to remove most of the pyridine. The crude material was purified directly by gradient elution on silica gel (RediSep-Rf-120 g, 0-15% MeOH/CH$_2$Cl$_2$, 30 minute gradient) to afford the product (mixture of two isomers plus impurities) as a foam. The mixture was purified by reverse phase chromatography (Phenominex Gemini 5 um C18 50×250 mm column; 20-50% CH$_3$CN in a 5 mM solution of NH$_4$HCO$_3$ over 30 min, 5 injections) and clean fractions were partitioned between dichloromethane and water. The aqueous phases were back-extracted once with dichloromethane. The combined organic phases were dried over Na$_2$SO$_4$, filtered and concentrated to afford Isomer 1A (faster eluting): $^1$H NMR (500 MHz, DMSO): δ(ppm) 8.14

(d, J=9.8 Hz, 2 H); 7.17 (s, 2 H); 5.06 (s, 1 H); 4.83-4.87 (m, 1 H); 4.15-4.27 (br m, 4 H); 3.88 (m, 2 H); 3.61 (m, 1 H); 3.51 (m, 1 H); 1.80 (m, 2 H); 1.58 (m, 6 H); 1.33 (d, J=4.0 Hz, 6 H); 1.22 (d, J=7.2 Hz, 3 H); 1.17 (dd, J=6.3, 3.5 Hz, 6 H); 1.06 (d, J=6.2 Hz, 2 H); 0.88 (d, J=6.7 Hz, 1 H); $^{31}$P NMR (243 MHz, CD$_3$OD): δ(ppm) 22.16; LC/MS: [(M+1)]$^-$=554.4; and Isomer 1B (slower eluting): $^1$H NMR (500 MHz, DMSO): δ(ppm) 8.14 (d, 9.1 Hz, 2 H); 7.17 (s, 2H); 5.07 (s, 1 H); 4.86 (t, J=6.3 Hz, 1 H); 4.36 (d, J=11.4 Hz, 1 H); 4.26 (d, J=14.3 Hz, 1 H); 4.19 (t, J=6.7 Hz, 1 H); 4.10 (d, J=10.3 Hz, 1 H); 3.95 (s, 1 H); 3.86 (br s, 1 H); 3.57 (d, J=8.6 Hz, 2 H); 1.81 (br s, 2 H); 1.55-1.63 (m, 6 H), 1.39 (s, 3 H); 1.35 (s, 3 H); 1.16-1.19 (m, 9 H); 1.05 (d, J=6.2 Hz, 3 H); $^-$P NMR (243 MHz, CD$_3$OD): δ(ppm) 22.06; LC/MS: [(M+1)]$^+$=554.4.

As noted above, absolute stereochemistry (R or S) of each of the separated stereoisomers was not determined. Therefore, A and B is not assigned to a particular IUPAC name.

EXAMPLE 2A/B

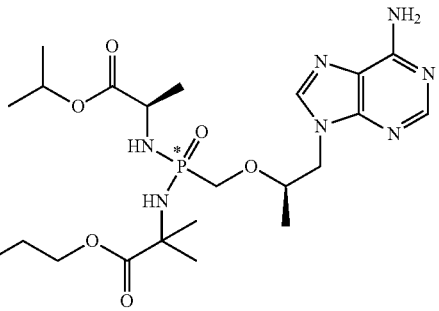

2A/B hexyl 2-((((S)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate; and hexyl 2-(((R)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate

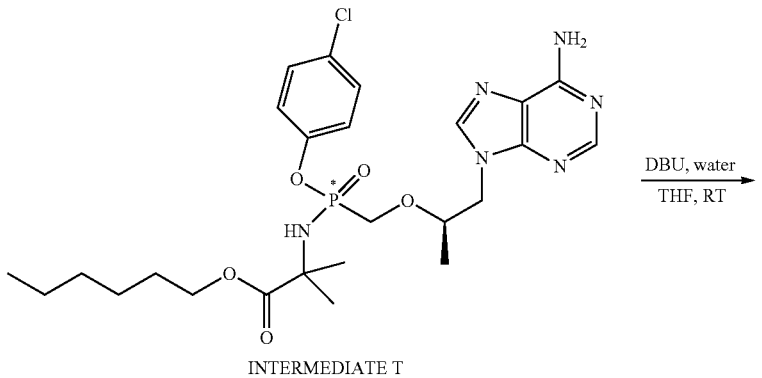

INTERMEDIATE T

DBU, water
THF, RT

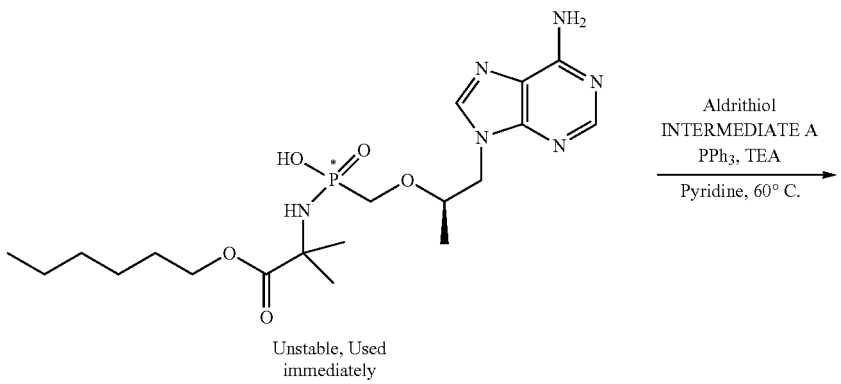

Unstable, Used immediately

Aldrithiol
INTERMEDIATE A
PPh$_3$, TEA

Pyridine, 60° C.

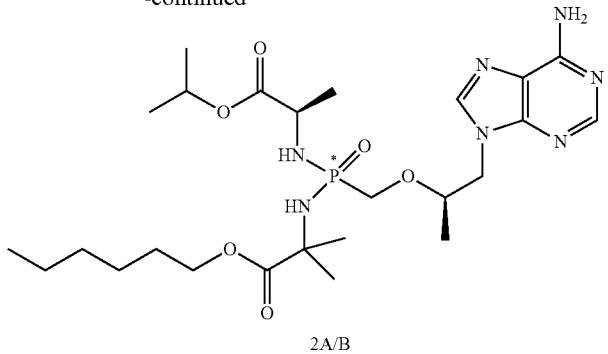

2A/B hexyl 2-((((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate (2A/B)

A mixture of INTERMEDIATE T (4 g, 7.05 mmol) and water (2.54 mL, 141 mmol) in tetrahydrofuran (20 mL) was treated with DBU (1.75 ml, 11.64 mmol) and stirred at room temperature for 2 hr. The mixture was concentrated and the residue was diluted with water (50 mL) and washed with CH$_2$Cl$_2$ (2×100 mL) to remove chlorophenol byproduct. The desired product stayed in the aqueous layer. The aqueous layer was concentrated azeotroping with MeCN (2×) and with toluene (1×), and was dried under high vacuum to afford the unstable intermediate: LC/MS: [(M+1)]$^+$=457.3. This intermediate was used immediately.

A mixture of the above intermediate (3.22 g, 7.05 mmol), INTERMEDIATE A (2.37 g, 14.11 mmol) and triethylamine (3.93 mL, 28.2 mmol) in pyridine (23.5 mL) was heated to 60° C. for 5 min, A freshly prepared solution of 2,2'-dipyridyl disulfide (Aldrithiol, 4.66 g, 21.16 mmol) and triphenylphosphine (5.55 g, 21.16 mmol) in pyridine (23.5 mL) was added to the mixture. The reaction was stirred at 60° C. overnight. The mixture was cooled to room temperature and concentrated to remove most of the pyridine. The crude material was purified directly by gradient elution on silica gel (RediSep-Rf-330 g, 0-15% MeOH/CH$_2$Cl$_2$, 35 minute gradient) to afford the product (mixture of two isomers plus impurities) as a foam. (1.3 g) The mixture was purified by reverse phase chromatography (XBridge 10 um C18 30×250 mm column; 30-65% CH$_3$CN in a 5 mM solution of NH$_4$HCO$_3$ over 30 min, 4 injections) and clean fractions were partitioned between CH$_2$Cl$_2$ and water. The aqueous phases were back-extracted once with CH$_2$Cl$_2$. The combined organic phases were dried over Na$_2$SO$_4$, filtered and concentrated to afford Isomer 2A (faster eluting): $^1$H NMR (500 MHz, DMSO): δ (ppm) 8.14 (d, J=13.0 Hz, 2 H); 7.17 (s, 2 H); 4.85-4.90 (m, 1 H); 4.13-4.29 (m, 4 H); 3.98-4.02 (m, 2 H); 3.92 (d. J=7.4 Hz, 1 H); 3.83 (d, J=10.6 Hz, 1 H); 3.61 (dd, J=12.9, 8.3 Hz, 1 H); 3.51 (dd, J=13.0, 8.8 Hz, 1 H); 1.51-1.57 (m, 2 H); 1.36 (s, 6 H); 1.23 (d, J=8.0 Hz, 8 H); 1.17 (dd, J=6.4, 3.2 Hz, 7 H); 1.06 (d, J 6.2 Hz, 3 H); 0.83 (d, J 7.4 Hz, 3 H); $^{31}$P NMR (243 MHz, CD$_3$OD): δ(ppm) 22.23; LC/MS: [(M+1)]$^+$=570.3; and Isomer 2B (slower eluting): $^1$H NMR (500 MHz, DMSO): δ(ppm) 8.14 (d, J=10.0 Hz, 2H); 7.17 (s, 2 H); 4.86-4.91 (m, 1 H); 4.35 (t, J=11.2 Hz, 1 H); 4.27 (dd, J=14.3, 4.0 Hz, 1 H); 4.16-4.20 (m, 2 H); 4.02 (t, J=6.5 Hz, 2 H); 3.92-3.95 (m, 1 H); 3.81-3.89 (m, 1 H); 3.57 (dd, J=8.6, 4.2 Hz, 2 H); 1.56 (p, J=7.0 Hz, 2 H); 1.39 (d, J=15.2 Hz, 6 H); 1.25 (s, 6 H); 1.18-1.20 (m, 9 H); 1.05 (d, J=6.2 Hz, 3 H); 0.84 (d, J=7.5 Hz, 3 H); $^{31}$P NMR (243 MHz, CD$_3$OD): δ(ppm) 22.07; LC/MS: [(M+1)]$^+$=570.3. As noted above, absolute stereochemistry (R or S) of each of the separated stereoisomers was not determined. Therefore, A and B is not assigned to a particular IUPAC name.

EXAMPLES 3-28

3A/B isopropyl 2-(((S)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate; and isopropyl 2-(((R)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate (3A/B)

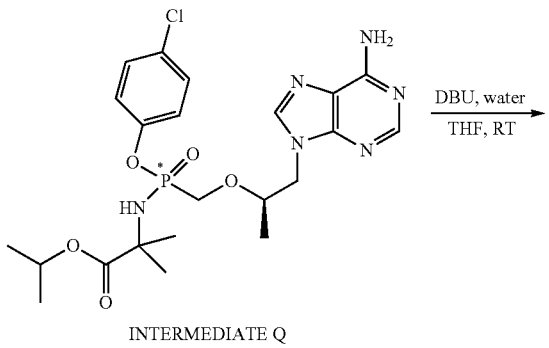

INTERMEDIATE Q

-continued

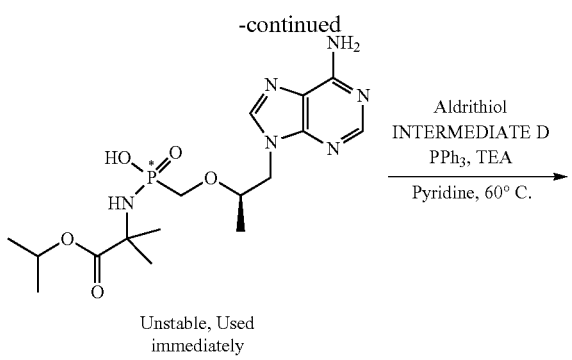

Aldrithiol
INTERMEDIATE D
PPh₃, TEA
Pyridine, 60° C.

Unstable, Used immediately

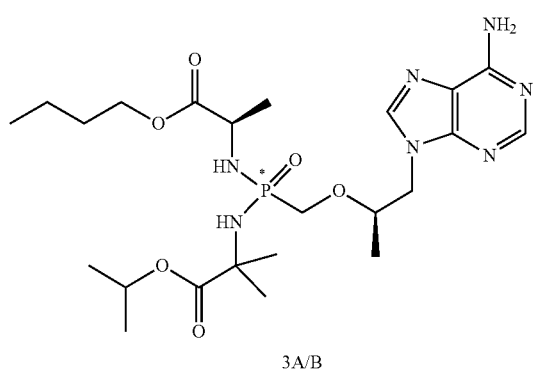

3A/B isopropyl 2-((((((R)-1-(6-amino-9H-purin-9-yl)propan-2-yl)oxy)methyl)(((R)-1-butoxy-1-oxopropan-2-yl)amino)phosphoryl)amino)-2-methylpropanoate (3A/B);

A mixture of INTERMEDIATE Q (10.3 g, 19.6 mmol) and water (7.07 ml, 392 mmol) in tetrahydrofuran (49 mL) was treated with DBU (3.11 mL, 20.6 mmol) and stirred at room temperature for 3 hr. The mixture was concentrated and the residue was diluted with water (300 mL) and washed with CHCl₃ (8×500 mL) to remove chlorophenol byproduct. The desired product stayed in the aqueous layer. The aqueous layer was concentrated azeotroping with acetonitrile twice and once with toluene and was dried under high vacuum to afford the unstable intermediate: LC/MS: [(M+1)]⁺=415.2. This intermediate was used immediately.

A mixture of the above intermediate (8,1 g, 19.5 mmol), INTERMEDIATE D (4.1 g, 22.5 mmol) and triethylamine (10.9 mL, 78.0 mmol) in pyridine (65 mL) was heated to 60° C. for 5 min. A freshly prepared solution of 2,2'-dipyridyl disulfide (Aldrithiol, 12.9 g, 58.6 mmol) and triphenylphosphine (15.4 g, 58.6 mmol) in pyridine (65 mL) was added to the mixture. The reaction was stirred at 60° C. overnight. The mixture was cooled to room temperature and concentrated to remove most of the pyridine. The crude material was purified directly by gradient elution on silica gel (RediSep-Rf-330 g, 0-15% MeOH/CH₂Cl₂, 30-min gradient) to afford the product (mixture of two isomers plus impurities) as a foam. The mixture was purified by reverse phase chromatography (Phenominex Gemini 5 um C18 50×250 mm column; 20-50% CH₃CN in a 5 mM solution of NH₄HCO₃ over 30 min, 5 injections) and clean fractions were partitioned between CH₂Cl₂ and water. The aqueous phases were back-extracted once with CH₂Cl₂. The combined organic phases were dried over Na₂SO₄, filtered and concentrated to afford Isomer 3A (faster eluting): ¹H NMR (500 MHz, DMSO): δ (ppm) 8.14 (d,=10.5 Hz, 2 H); 7.17 (s, 2 H); 4.81-4.86 (m, 1 H); 4.26 (t, J=11.4 Hz, 2 H); 4.14-4.18 (m, 2 H); 3.98-4.07 (m, 2 H); 3.91 (m, 1 H); 3.61 (dd, J=12.9, 8.4 Hz, 1 H); 3.51 (dd, J=12.8, 8.8 Hz, 2 H); 1.54 (p, J=7.1 Hz, 2 H); 1.29-1.34 (m, 8 H); 1.25 (d, J=7.1 Hz, 3 H), 1.17 (dd, J=6.3, 2.9 Hz, 6 H); 1.06 (d, J=6.2 Hz, 3 H); 0.87 (t, J=7.4 Hz, 3 H); ³¹P NMR (243 MHz, CD₃OD): δ(ppm) 22.16; LC/MS: [(M+1)]⁺=542.3; and isomer 3B (slower eluting): ¹H NMR (500 MHz, DMSO): δ(ppm) 8.14 (d, J=9.4 Hz, 2 H); 7.17 (s, 2 H); 4.83-4.88 (m, 1 H); 4.40 (t, J=11.3 Hz, 1 H); 4.26 (dd, J=14.3, 4.0 Hz, 1 H); 4.18 (dd, J=14.5, 5.9 Hz, 1 H); 4.13 (d, J=10.3 Hz, 1 H); 4.02-4.07 (m, 2 H); 3.88-3.96 (m, 2 H); 3.55-3.58 (m, 2 H); 1.52-1.58 (m, 2 H); 1.39 (s, 3 H); 1.35 (s, 3 H); 1.30-1.33 (m, 3 H); 1.16-1.21 (m, 8 H); 1.05 (d, J=6.2 Hz, 3 H); 0.88 (t, J=7.4 Hz, 3 H); ³¹P NMR (243 MHz, CD₃OD): -δ(ppm) 22.04; LC/MS: [(M+1)]⁺=542.3. As noted above, absolute stereochemistry (R or S) of each of the separated stereoisomers was not determined. Therefore, A and B is not assigned to a particular IUPAC name.

The compounds in Table 1 were prepared in an analogous fashion to that described for the examples above. The isomers were separated by preparative HPLC or/and preparative chiral SFC.

TABLE 1

| Compound | Structure | Name | LC/MS (M + 1)⁺ |
| --- | --- | --- | --- |
| 4A/B | 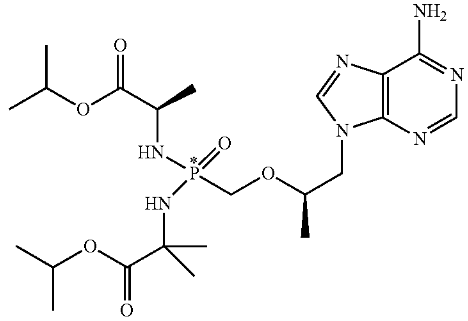 [SMILES: CC(C)OC(=O)[C@@H](C)NP(=O)(CO[C@H](C)Cn1cnc2c(N)ncnc21)NC(C)(C)C(=O)OC(C)C] | isopropyl 2-(((S)-(((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate and isopropyl 2-(((R)-(((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate | 528.3 and 528.3 |

TABLE 1-continued

| Compound | Structure | Name | LC/MS (M + 1)+ |
|---|---|---|---|
| 5A/B | 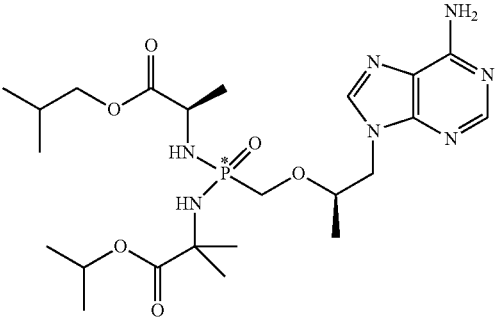 [SMILES: CC(C)COC(=O)[C@@H](C)NP(=O)(CO[C@H](C)Cn1cnc2c(N)ncnc21)NC(C)(C)C(=O)OC(C)C] | isopropyl 2-(((S)-((((R)-1-(6-amino-9H-purin-9-yl)propan-2-yl)oxy)methyl)(((R)-1-isobutoxy-1-oxopropan-2-yl)amino)phosphoryl)amino)-2-methylpropanoate and isopropyl 2-(((R)-((((R)-1-(6-amino-9H-purin-9-yl)propan-2-yl)oxy)methyl)(((R)-1-isobutoxy-1-oxopropan-2-yl)amino)phosphoryl)amino)-2-methylpropanoate | 542.3 and 542.3 |
| 6A/B | 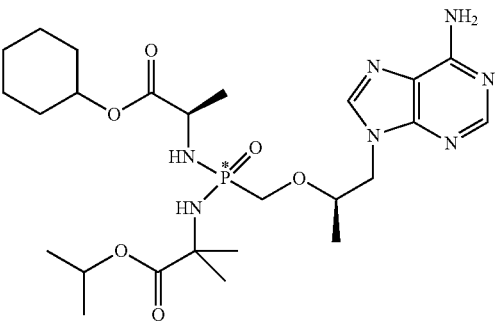 [SMILES: CC(C)OC(=O)C(C)(C)NP(=O)(CO[C@H](C)Cn1cnc2c(N)ncnc21)N[C@H](C)C(=O)OC1CCCCC1] | isopropyl 2-(((S)-((((R)-1-(6-amino-9H-purin-9-yl)propan-2-yl)oxy)methyl)(((R)-1-(cyclohexyloxy)-1-oxopropan-2-yl)amino)phosphoryl)amino)-2-methylpropanoate and isopropyl 2-(((R)-((((R)-1-(6-amino-9H-purin-9-yl)propan-2-yl)oxy)methyl)(((R)-1-(cyclohexyloxy)-1-oxopropan-2-yl)amino)phosphoryl)amino)-2-methylpropanoate | 568.3 and 568.3 |
| 7A/B | 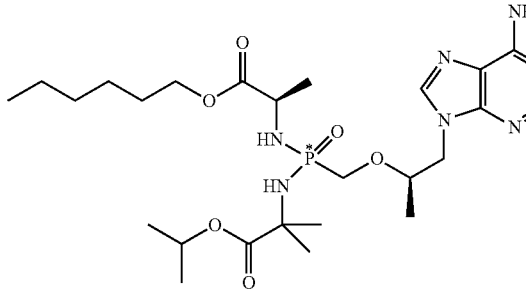 | isopropyl 2-(((S)-((((R)-1-(6-amino-9H-purin-9-yl)propan-2-yl)oxy)methyl)(((R)-1-(hexyloxy)-1-oxopropan-2-yl)amino)phosphoryl)amino)-2-methylpropanoate and isopropyl 2-(((R)-((((R)-1-(6-amino-9H-purin-9-yl)propan-2-yl)oxy)methyl)(((R)-1-(hexyloxy)-1-oxopropan-2-yl)amino)phosphoryl)amino)-2-methylpropanoate | 570.3 and 570.4 |
| 8A/B | 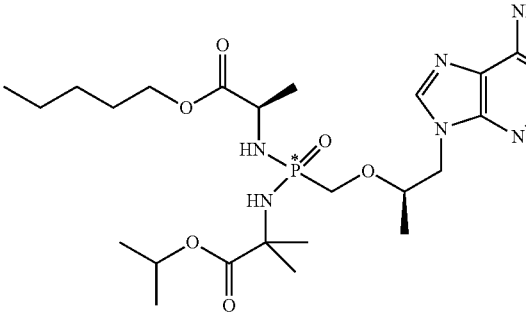 | isopropyl 2-(((S)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate and isopropyl 2-(((R)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate | 556.4 and 556.4 |

TABLE 1-continued

| Compound | Structure | Name | LC/MS (M + 1)+ |
|---|---|---|---|
| 9A/B | 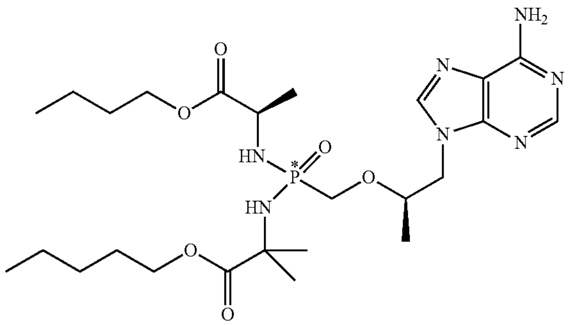 [SMILES: CCCCCOC(=O)C(C)(C)NP(=O)(CO[C@H](C)Cn1cnc2c(N)ncnc21)N[C@H](C)C(=O)OCCCC] | pentyl 2-(((S)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate and pentyl 2-(((R)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate | 570.3 and 570.3 |
| 10A/B | 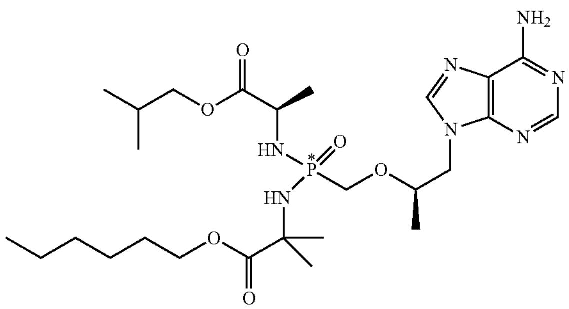 [SMILES: CCCCCCOC(=O)C(C)(C)NP(=O)(CO[C@H](C)Cn1cnc2c(N)ncnc21)N[C@H](C)C(=O)OCC(C)C] | hexyl 2-(((S)-((((R)-1-(6-amino-9H-purin-9-yl)propan-2-yl)oxy)methyl)(((R)-1-isobutoxy-1-oxopropan-2-yl)amino)phosphoryl)amino)-2-methylpropanoate and hexyl 2-(((R)-((((R)-1-(6-amino-9H-purin-9-yl)propan-2-yl)oxy)methyl)(((R)-1-isobutoxy-1-oxopropan-2-yl)amino)phosphoryl)amino)-2-methylpropanoate | 584.4 and 584.4 |
| 11A/B | 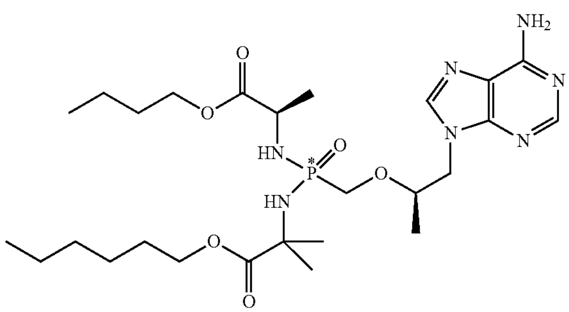 [SMILES: CCCCCCOC(=O)C(C)(C)NP(=O)(CO[C@H](C)Cn1cnc2c(N)ncnc21)N[C@H](C)C(=O)OCCCC] | hexyl 2-(((S)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate and hexyl 2-(((R)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate | 584.4 and 584.4 |
| 12A/B | 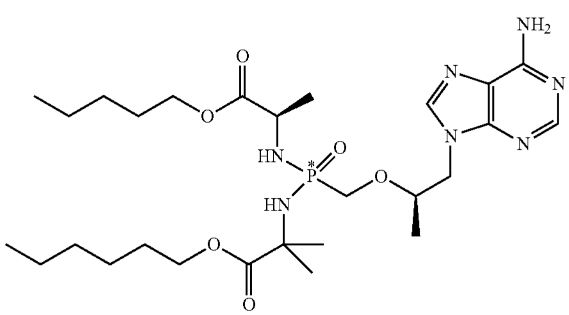 [SMILES: CCCCCCOC(=O)C(C)(C)NP(=O)(CO[C@H](C)Cn1cnc2c(N)ncnc21)N[C@H](C)C(=O)OCCCCC] | hexyl 2-(((S)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate and hexyl 2-(((R)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate | 598.4 and 598.4 |
| 13A/B | 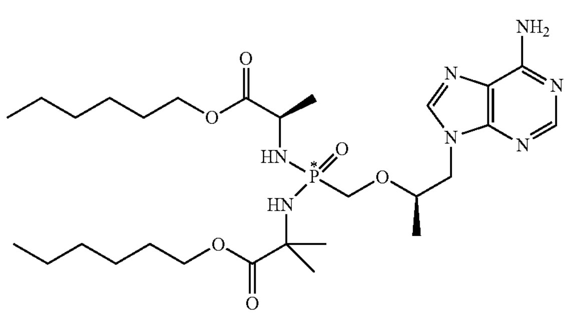 [SMILES: CCCCCCOC(=O)[C@@H](C)NP(=O)(CO[C@H](C)Cn1cnc2c(N)ncnc21)NC(C)(C)C(=O)OCCCCCC] | hexyl 2-(((S)-((((R)-1-(6-amino-9H-purin-9-yl)propan-2-yl)oxy)methyl)(((R)-1-(hexyloxy)-1-oxopropan-2-yl)amino)phosphoryl)amino)-2-methylpropanoate and hexyl 2-(((R)-((((R)-1-(6-amino-9H-purin-9-yl)propan-2-yl)oxy)methyl)(((R)-1-(hexyloxy)-1-oxopropan-2-yl)amino)phosphoryl)amino)-2-methylpropanoate | 612.4 and 612.4 |

TABLE 1-continued

| Compound | Structure | Name | LC/MS (M + 1)+ |
|---|---|---|---|
| 14A/B | 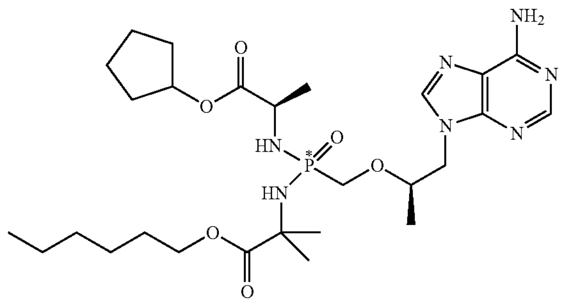 [SMILES: CCCCCCOC(=O)C(C)(C)NP(=O)(CO[C@H](C)Cn1cnc2c(N)ncnc21)N[C@H](C)C(=O)OC1CCCC1] | hexyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate and hexyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate | 596.4 and 596.4 |
| 15A/B | 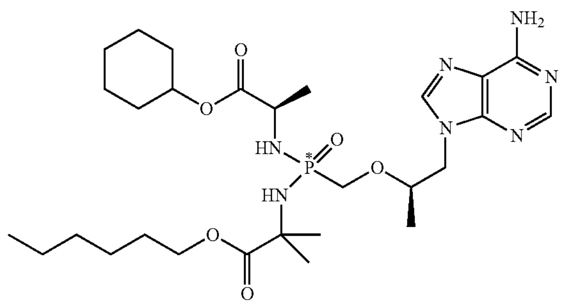 [SMILES: CCCCCCOC(=O)C(C)(C)NP(=O)(CO[C@H](C)Cn1cnc2c(N)ncnc21)N[C@H](C)C(=O)OC1CCCCC1] | hexyl 2-(((S)-((((R)-1-(6-amino-9H-purin-9-yl)propan-2-yl)oxy)methyl)(((R)-1-(cyclohexyloxy)-1-oxopropan-2-yl)amino)phosphoryl)amino)-2-methylpropanoate and hexyl 2-(((R)-((((R)-1-(6-amino-9H-purin-9-yl)propan-2-yl)oxy)methyl)(((R)-1-(cyclohexyloxy)-1-oxopropan-2-yl)amino)phosphoryl)amino)-2-methylpropanoate | 610.4 and 610.4 |
| 16A/B | 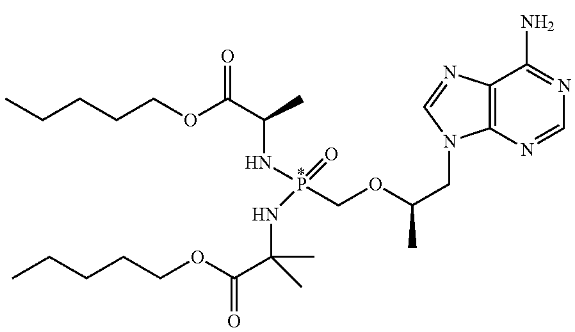 [SMILES: CCCCCOC(=O)[C@@H](C)NP(=O)(CO[C@H](C)Cn1cnc2c(N)ncnc21)NC(C)(C)C(=O)OCCCCC] | pentyl 2-(((S)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate and pentyl 2-(((R)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate | 584.4 and 584.4 |
| 17A/B | 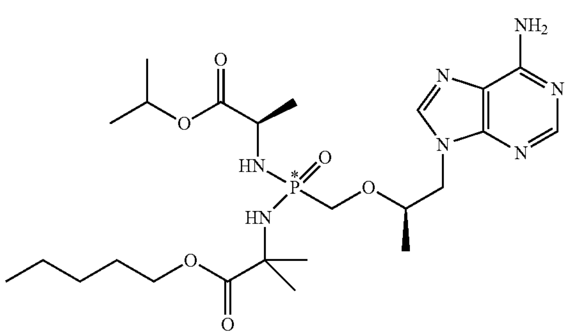 [SMILES: CCCCCOC(=O)C(C)(C)NP(=O)(CO[C@H](C)Cn1cnc2c(N)ncnc21)N[C@H](C)C(=O)OC(C)C] | pentyl 2-(((S)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate and pentyl 2-(((R)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate | 556.3 and 556.3 |

TABLE 1-continued

| Compound | Structure | Name | LC/MS (M + 1)+ |
|---|---|---|---|
| 18A/B | 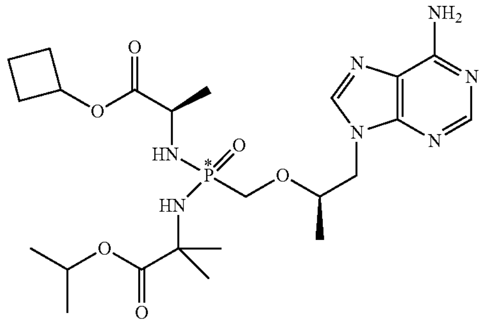 [SMILES: CC(C)OC(=O)C(C)(C)NP(=O)(CO[C@H](C)Cn1cnc2c(N)ncnc21)N[C@H](C)C(=O)OC1CCC1] | isopropyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate and isopropyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate | 540.2 and 540.2 |
| 19A/B | 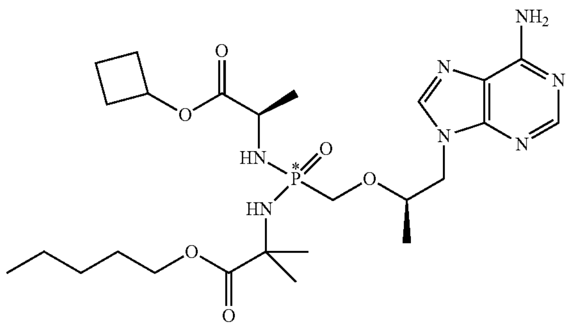 [SMILES: CCCCCOC(=O)C(C)(C)NP(=O)(CO[C@H](C)Cn1cnc2c(N)ncnc21)N[C@H](C)C(=O)OC1CCC1] | pentyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate and pentyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate | 568.4 and 568.4 |
| 20A/B | 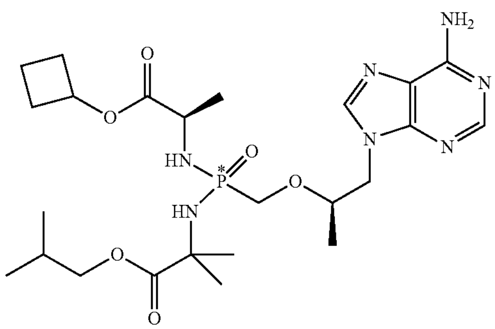 [SMILES: CC(C)COC(=O)C(C)(C)NP(=O)(CO[C@H](C)Cn1cnc2c(N)ncnc21)N[C@H](C)C(=O)OC1CCC1] | isobutyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate and isobutyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate | 554.2 and 554.2 |
| 21A/B | 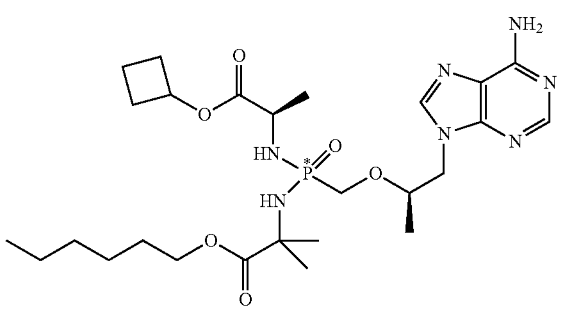 [SMILES: CCCCCCOC(=O)C(C)(C)NP(=O)(CO[C@H](C)Cn1cnc2c(N)ncnc21)N[C@H](C)C(=O)OC1CCC1] | hexyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate and hexyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate | 582.2 and 582.2 |
| 22A/B | 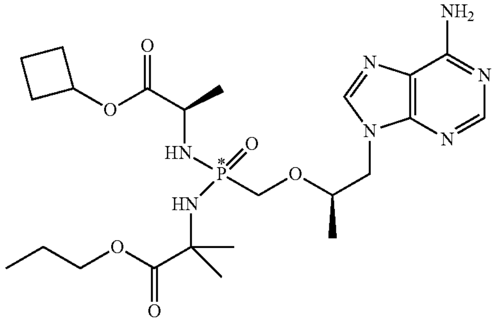 [SMILES: CCCOC(=O)C(C)(C)NP(=O)(CO[C@H](C)Cn1cnc2c(N)ncnc21)N[C@H](C)C(=O)OC1CCC1] | propyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate and propyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate | 540.2 and 540.2 |

TABLE 1-continued

| Compound | Structure | Name | LC/MS (M + 1)+ |
|---|---|---|---|
| 23A/B | 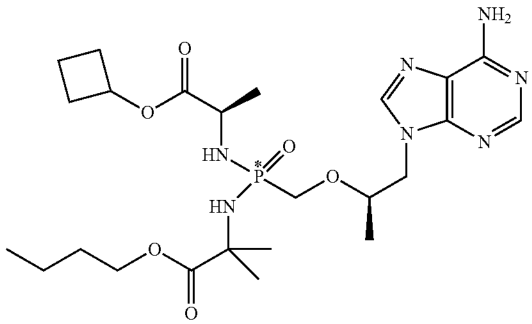 [SMILES: CCCCOC(=O)C(C)(C)NP(=O)(CO[C@H](C)Cn1cnc2c(N)ncnc21)N[C@H](C)C(=O)OC1CCC1] | butyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate and butyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate | 554.2 and 554.2 |
| 24A/B | 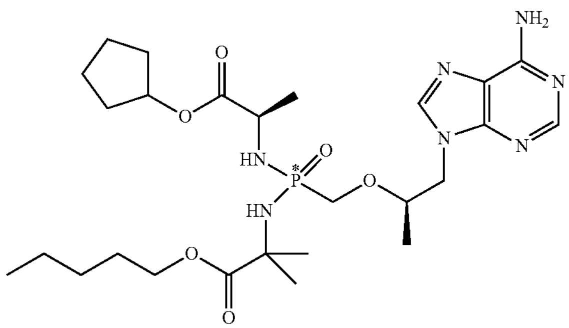 [SMILES: CCCCCOC(=O)C(C)(C)NP(=O)(CO[C@H](C)Cn1cnc2c(N)ncnc21)N[C@H](C)C(=O)OC1CCCC1] | pentyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate and pentyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate | 582.4 and 582.4 |
| 25A/B | 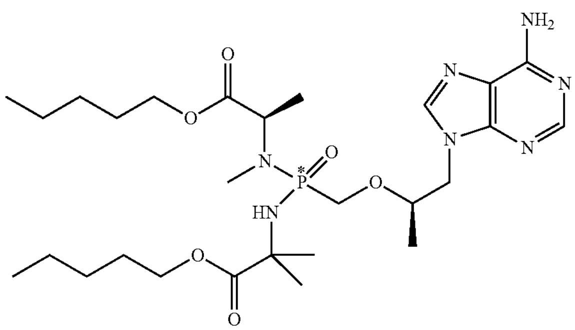 [SMILES: CCCCCOC(=O)[C@@H](C)N(C)P(=O)(CO[C@H](C)Cn1cnc2c(N)ncnc21)NC(C)(C)C(=O)OCCCCC] | pentyl 2-(((S)-((((R)-1-6-amino-9H-purin-9-yl)propan-2-yl)oxy)methyl)(methyl((R)-1-oxo-1-(pentyloxy)propan-2-yl)amino)phosphoryl)amino)-2-methylpropanoate and pentyl 2-(((R)-((((R)-1-(6-amino-9H-purin-9-yl)propan-2-yl)oxy)methyl)(methyl((R)-1-oxo-1-(pentyloxy)propan-2-yl)amino)phosphoryl)amino)-2-methylpropanoate | 598.4 and 598.4 |
| 26A/B | 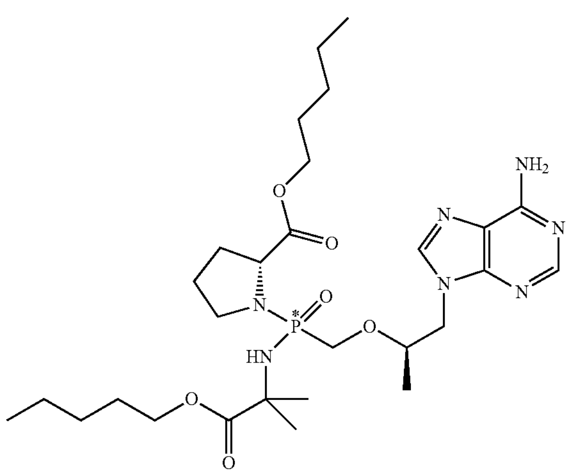 [SMILES: CCCCCOC(=O)[C@H]1CCCN1P(=O)(CO[C@H](C)Cn1cnc2c(N)ncnc21)NC(C)(C)C(=O)OCCCCC] | pentyl (((S)-(((R)-1-(6-amino-9H-purin-9-yl)propan-2-yl)oxy)methyl)((2-methyl-1-oxo-1-(pentyloxy)propan-2-yl)amino)phosphoryl)-D-prolinate and pentyl (((R)-(((R)-1-(6-amino-9H-purin-9-yl)propan-2-yl)oxy)methyl)((2-methyl-1-oxo-1-(pentyloxy)propan-2-yl)amino)phosphoryl)-D-prolinate | 610.4 and 610.4 |

TABLE 1-continued

| Compound | Structure | Name | LC/MS (M + 1)+ |
|---|---|---|---|
| 27A/B | 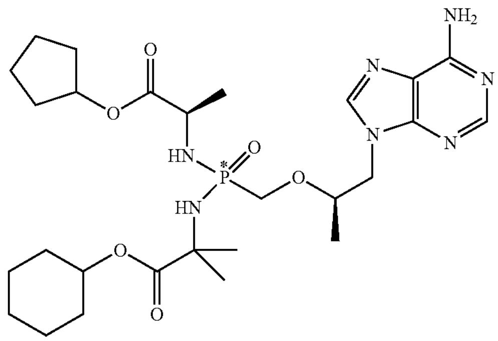 [SMILES: C[C@H](Cn1cnc2c(N)ncnc21)OCP(=O)(N[C@H](C)C(=O)OC1CCCC1)NC(C)(C)C(=O)OC1CCCCC1] | cyclohexyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate and cyclohexyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate | 594.4 and 594.3 |
| 28A/B | 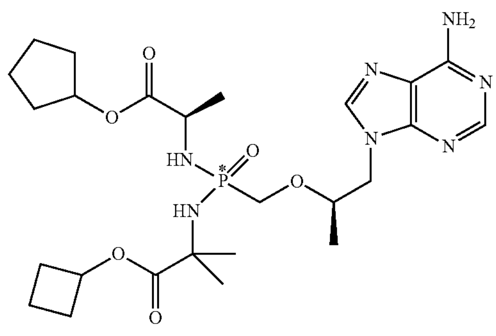 [SMILES: C[C@H](Cn1cnc2c(N)ncnc21)OCP(=O)(N[C@H](C)C(=O)OC1CCCC1)NC(C)(C)C(=O)OC1CCC1] | cyclobutyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate and cyclobutyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate | 566.3 and 566.3 |

As noted above, absolute stereochemistry (R or S) of each of the separated stereoisomers was not determined. Therefore, A and B is not assigned to a particular IUPAC name in this table.

EXAMPLE 29

Assessing Antiviral Potency in a Multiple Round HIV-1 Infection Assay (Viking Assay)

The antiviral activity of the tenofovir prodrugs of the Examples herein was assessed in an assay that measures the rate of replication of HIV in cell culture, termed the Viking assay (VIral KINetics in Green cells) and performed as follows. HIV-1 replication was monitored using MT4-gag-GFP clone D3 (hereafter designated MT4-GFP; GFP is green fluorescent protein), which are MT-4 cells modified to harbor a GFP reporter gene, the expression of which is dependent on the HIV-1 expressed proteins tat and rev; see Wang Y-J et al., 2010 *J Virological Methods* 165:230-237. Productive infection of an MT4-GFP cell with HIV-1 results in GFP expression approximately 24 h post-infection. MT4-GFP cells were maintained at 37° C./5% $CO_2$/90% relative humidity in RPMI 1640 supplemented with 10% fetal bovine serum, 100 U/ml penicillin/streptomycin, and 400 µg/ml G418 to maintain the reporter gene. For infections, MT4-GFP cells were placed in the same medium lacking G418 and infected overnight with HIV-1 (H9/IIIB strain) virus at an approximate multiplicity of infection of 0.01 in the same incubation conditions. Cells were then washed and re-suspended in either RPMI 1640 supplemented with 10% or 50% normal human serum (NHS) at $1.6 \times 10^5$ cells/mL (10% NHS or 50% NHS, respectively). Compound plates were prepared by dispensing compounds dissolved in DMSO into wells of 384 well poly-D-lysine-coated plates (0.2 µl/well) using an ECHO acoustic dispenser. Each compound was tested in a 10-point serial 3-fold dilution (typical final concentrations: 8.4 µM-0.42 nM). Controls included no inhibitor (DMSO only) and a combination of three antiviral agents (efavirenz, indinavir, and an integrase strand transfer inhibitor at final concentrations of 4 µM each). Cells were added (50 µL/well) to compound plates and the infected cells were maintained at 37'C/5% CO2/90% relative humidity.

Infected cells were quantified at two time points, ~48 h and ~72 h post-infection, by counting the number of green cells in each well using an Acumen eX3 scanner. The increase in the number of green cells over ~24 h period gives the reproductive ratio, R0, which is typically 5-15 and has been shown experimentally to be in logarithmic phase (data not shown). R0 is calculated for each well, and $IC_{50}$s determined by non-linear 4-parameter curve fitting. Assay $IC_{50}$ results are shown in Table 2.

EXAMPLE 30

Prodrug Stability Assay in Bio-relevant Media

The following assay was employed to evaluate the stability of the prodrugs in simulated gastrointestinal tract conditions. Preparation of fasted state simulated intestinal fluid (FaSSIF) using Phares SIF Powder was carried out according to protocols from Phare Drug Delivery AG (Baselland, Switzerland). For sample preparation, 10 µL stock solutions (10 mM) of prodrug substance in DMSO was added to 990 µL of 0.5 mg/mL Pancreatin solution (Fisher CAS#8049-47-6) in FaSSIF. Two samples were prepared for each compound. If the sample was a clear solution, it was directly analyzed by HPLC. If the sample was not clear, the sample was diluted with 100% ACN, maintained at 37° C.

and observed 5 h later. If the sample was clear, HPLC analysis was directly performed. If the sample was still not clear, the sample was diluted with 100% ACN and assayed by HPLC. All the samples were vortexed for 3 min and observed before injection. For the diluted samples, the area is multiplied by a factor when the data is analyzed. The analysis was carried out with an Agilent 1100 series HPLC with autosampler. The column was usually a Poroshell 120 EC-C18, 4.6×50 mm, 2.7 µm. The flow rate was 1.8 mL/min, and the injection volume was 5 or 10 µL. UV detection was in the range 210-400 nm. The mobile phase consisted of solvent A (water plus 10 mM tetrabutylammonium bromide) and solvent B (acetonitrile) with a gradient of 90% solvent A at 0 min, changing to 95% solvent B over 6 min, maintaining for 1.5 min, then reverting to 90% solvent A over 1.6 min. The HPLC peak area of the prodrug at 5 h was divided by the HPLC peak area of the prodrug at 0 h, to generate the % claimed parent ratio, which is summarized in Table 2. for GI Tract stability.

EXAMPLE 31

Pharmacokinetic Studies in Dogs—In Vivo Dog PK

Prodrugs were administered to beagle dogs through intravenous (IV) and oral (P.O.) administrations in a non-crossover manner. The IV dose was prepared in 20% hydroxypropyl β-cyclodextrin (HPBCD) and was administered at 1 mg/kg QD via the cephalic or saphenous vein. The P.O. dose was prepared in 10% polysorbate 80 (Tween 80) and was administered at 10 mg/kg QD via gavage.

Blood samples were serially collected following dose administration for up to 48 hr and plasma was separated by centrifugation. The concentrations of prodrugs in dog plasma were determined by a LC-MS/MS assay following a protein precipitation step and addition of an appropriate internal standard (labetalol, imipramine or diclofenac). Quantification was done by determining peak area-ratios of the prodrugs and tenofovir to the internal standard. Additional blood sample(s) was collected following dose administration for up to 24 hr. Peripheral blood mononuclear cells (PRNICs) were isolated by centrifugation, using tubes and reagents specified for the application. The concentrations of tenofovir and/or its phosphate conjugate(s) in PBMCs were determined by an LC-MS/MS assay following a protein precipitation step and addition of an appropriate internal standard (labetalol, imipramine or diclofenac). Quantification was done by determining peak area-ratios of tenofovir and/or its phosphate conjugate(s) to the internal standard.

Pharmacokinetic parameters were obtained using non-compartmental methods (Watson®). The area under the plasma concentration-time curve ($AUC_{0-t}$) was calculated from the first time point (0 min) up to the last time point with measurable drug concentration using the linear trapezoidal or linear/log-linear trapezoidal rule. The IV plasma clearance was calculated by dividing the dose by $AUC_{0-inf}$. The terminal half-life of elimination was determined by unweighted linear regression analysis of the log-transformed data. The time points for determination of half-life were selected by visual inspection of the data. The volume of distribution at steady state ($Vd_{ss}$) was obtained from the product of plasma clearance and mean residence time (determined by dividing the area under the first moment curve by the area under the curve). The maximum plasma concentration ($C_{max}$) and the time at which maximum concentration occurred ($T_{max}$) were obtained by inspection of the plasma concentration-time data. Absolute oral bioavailability (% F) was determined from dose-adjusted IV and P.O. AUC ratios of the prodrug.

Without wishing to be bound by theory, it is believed that the compounds of

Formula I are converted by one or more mechanisms to the corresponding monophosphate or diphosphate of tenofovir. In vivo, tenofovir (TFV) is phosphorylated intracellularly to its active anabolite, tenofovir diphosphate (TFV-DP), which suppresses viral replication via inhibiting the activity of HIV reverse transcriptase to impart antiviral efficacy. Table 2 shows in vivo dog PK data in the form of TFV-DP concentrations (µM) in dog PRMCs at 24 h following a 10 mg/kg P.O. dose of the indicated prodrug.

TABLE 2

| Example | Viking, IC50 (10% NHS) (nM) | Viking, IC50 (50% NHS) (nM) | GI Tract stability (%) | In Vivo Dog PK (µM) |
|---|---|---|---|---|
| 1A | 19.3 | 44.3 | | |
| 1B | 2.4 | 6.2 | 95.9 | 24.5 |
| 2A | 15.9 | 78 | 100 | 31.0 |
| 2B | 1.3 | 5.2 | 94.2 | 18.2 |
| 3A | 20.7 | 71.4 | | |
| 3B | 3.8 | 20.5 | 95.6 | 15.3 |
| 4A | 417.8 | 1396 | | |
| 4B | 74.6 | 122.3 | | |
| 5A | 33.1 | 129.4 | | |
| 5B | 2.5 | 6.4 | | 10.7 |
| 6A | 100.6 | 500.5 | | |
| 6B | 1.9 | 5.6 | | 11.7 |
| 7A | 10.4 | 57.8 | | |
| 7B | 4.7 | 28.8 | | |
| 8A | 12.6 | 41.4 | | |
| 8B | 3.9 | 20.7 | | |
| 9A | 6.1 | 19.8 | 100 | |
| 9B | 1.0 | 4.2 | 73.9 | |
| 10A | 6.6 | 72.5 | | |
| 10B | 0.7 | 2.0 | 66.8 | |
| 11A | 9.9 | 99.0 | | |
| 11B | 0.8 | 2.6 | | |
| 12A | 7.3 | 54.4 | | |
| 12B | 0.5 | 3.3 | | |
| 13A | 7.2 | 40.4 | 99.1 | |
| 13B | | | 83.8 | |
| 14A | 9.8 | 67.2 | | |
| 14B | 0.6 | 2.0 | 47.2 | |
| 15A | 7.7 | 25.9 | | |
| 15B | 0.7 | 2.1 | 51.2 | |
| 16A | 10.0 | 60.1 | | |
| 16B | 0.9 | 4.2 | 97.8 | |
| 17A | 15.9 | 78.0 | 100 | |
| 17B | 1.3 | 5.2 | 94.2 | |
| 18A | 20.0 | 34.2 | | |
| 18B | 11.0 | 25.8 | 97.4 | 26.5 |
| 19A | 6.9 | 27.4 | | |
| 19B | 2.5 | 10.8 | 49.3 | |
| 20A | 5.9 | 17.4 | 98.1 | |
| 20B | 1.7 | 5.9 | 71.0 | |
| 21A | 4.4 | 14.9 | | |
| 21B | 0.7 | 2.8 | | |
| 22A | 11.6 | 50.9 | 98.2 | 18.8 |
| 22B | 4.4 | 15.4 | 72.6 | 16.0 |
| 23A | 6.7 | 35.5 | | |
| 23B | 6.0 | 13.6 | 58.6 | |
| 24A | 3.2 | 30.6 | 97.8 | |
| 24B | 0.9 | 3.9 | 82.7 | 13.0 |
| 25A | | | | |
| 25B | 3.6 | 9.6 | 94.4 | |
| 26A | 5.3 | 50.3 | | |
| 26B | 4.4 | 19.5 | 92.5 | |
| 27A | 12.9 | 64.5 | | |
| 27B | 1.6 | 4.7 | 93.5 | |
| 28A | 5.4 | 16.1 | | |
| 28B | 2.7 | 3.3 | 90.2 | |

What is claimed is:

1. A compound of structural Formula I:

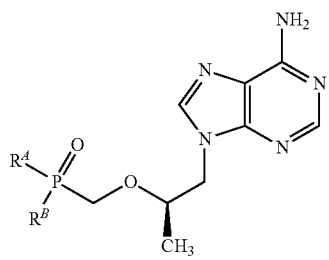

or pharmaceutically acceptable salt thereof, wherein:
$R^A$ is a D-proline ester residue of formula (ii):

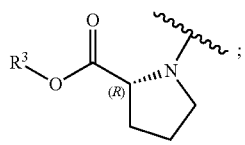

$R^3$ is
(a) —$C_{1-10}$alkyl unsubstituted or substituted with one to three substituents independently selected from fluoro, chloro, bromo, —$OR^7$, —SH, —$NR^8R^9$, —$C_{3-6}$cycloalkyl or spiro—$C_{3-6}$cycloalkyl,
(b) —$CH_2$-phenyl unsubstituted or substituted with one to three substituents independently selected from fluoro, chloro, bromo, —$OR^{10}$, —SH, —$NR^8R^9$ or —$C_{1-3}$alkyl,
(c) —$C_{3-8}$cycloalkyl unsubstituted or substituted with one to three substituents independently selected from fluoro, chloro, bromo, —$OR^{10}$, —SH, —$NR^8R^9$ or —$C_{1-3}$alkyl,
(d) aryl unsubstituted or substituted with one to three substituents independently selected from fluoro, chloro, bromo, —$OR^{10}$, —SH, —$NR^8R^9$ or —$C_{1-3}$alkyl,
(e) —$C_{1-5}$alkyl-X—$C_{1-5}$alkyl wherein X is O, S or NH,
(f) heteroaryl unsubstituted or substituted with one to three substituents independently selected from fluoro, chloro, bromo, —$OR^{10}$, —SH, —$NR^8R^9$ or —$C_{1-3}$alkyl, or
(g) a heterocyclic ring unsubstituted or substituted with one to three substituents independently selected from fluoro, chloro, bromo, —$OR^{10}$, —SH, —$NR^8R^9$ or —$C_{1-3}$alkyl;

$R^B$ is a geminally di-substituted amino acid ester residue of formula (iii):

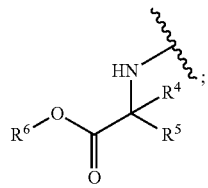

$R^4$ and $R^5$ are each independently selected from (a) —$C_{1-4}$alkyl, (b) —$C_{1-4}$alkyl substituted with —OH, —SH, —$SCH_3$, —$NH_2$, —NH—C(=NH)—$NH_2$, (c) —$CH_2$-phenyl, (d) —$CH_2$-phenol, (e) —$(CH_2)_{1-2}$—COOH, (f) —$(CH_2)_{1-2}$—$CONH_2$, (g) —$CH_2$-1H-indole, (h) —$CH_2$-imidazole, (i) aryl, or (j) heteroaryl;

or $R^4$ and $R^5$ are joined together with the carbon to which they are both attached to form —$C_{3-6}$cycloalkyl or a 4 to 6-membered heterocyclic ring;

$R^6$ is
(a) —$C_{1-10}$alkyl unsubstituted or substituted with one to three substituents independently selected from fluoro, chloro, bromo, —$OR^{11}$, —SH, —$NR^{12}R^{13}$, —$C_{3-6}$cycloalkyl or spiro-$C_{3-6}$cycloalkyl,
(b) —$CH_2$-phenyl unsubstituted or substituted with one to three substituents independently selected from fluoro, chloro, bromo, —$OR^{14}$, —SH, —$NR^{12}R^{13}$, —$C_{1-3}$alkyl,
(c) —$C_{3-8}$cycloalkyl unsubstituted or substituted with one to three substituents independently selected from fluoro, chloro, bromo, —$OR^{14}$, —SH, —$NR^{12}R^{13}$ or —$C_{1-3}$alkyl,
(d) aryl unsubstituted or substituted with one to three substituents independently selected from fluoro, chloro, bromo, —$OR^{14}$, —SH, —$NR^{12}R^{13}$ or —$C_{1-3}$alkyl,
(e) —$C_{1-5}$alkyl-X—$C_{1-5}$alkyl wherein X is O, S or NH;
(f) heteroaryl unsubstituted or substituted with one to three substituents independently selected from fluoro, chloro, bromo, —$OR^{14}$, —SH, —$NR^{12}R^{13}$ or —$C_{1-3}$alkyl, or
(g) a heterocyclic ring unsubstituted or substituted with one to three substituents independently selected from fluoro, chloro, bromo, —$OR^{14}$, —SH, —$NR^{12}R^{13}$ or —$C_{1-3}$alkyl;

$R^7$ and $R^{11}$ are each independently selected from —H or —$C_{3-6}$cycloalkyl;
$R^8$ and $R^9$ are each independently selected from —H, —$C_{1-3}$alkyl or —$C_{3-6}$cycloalkyl;
$R^{12}$ and $R^{13}$ are each independently selected from —H, —$C_{1-3}$alkyl or —$C_{3-6}$cycloalkyl; and
$R^{10}$ and $R^{14}$ are each independently selected from —H, —$C_{1-3}$alkyl or —$C_{3-6}$cycloalkyl.

2. A compound which is selected from the following:

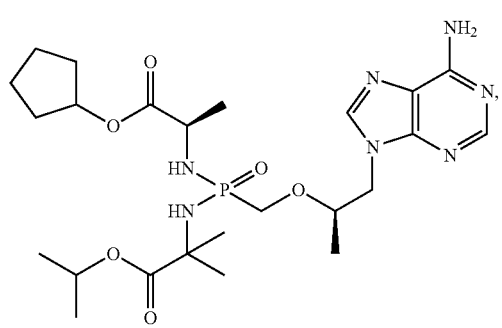

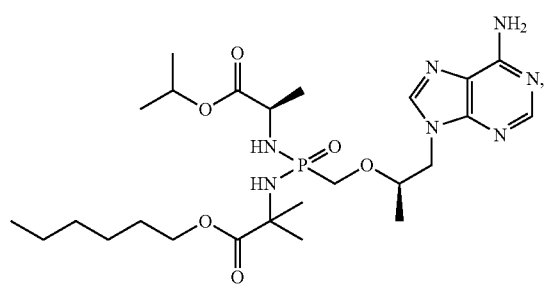
2
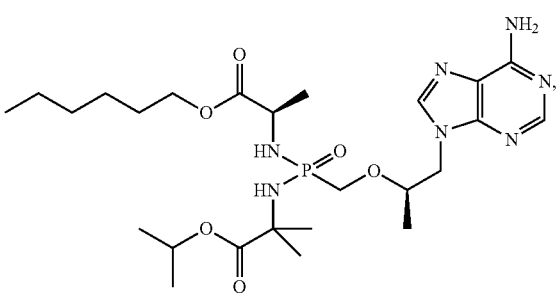
7
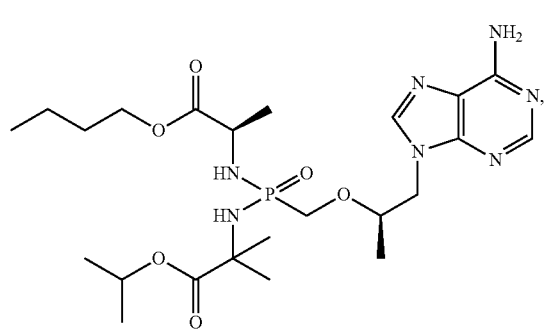
3
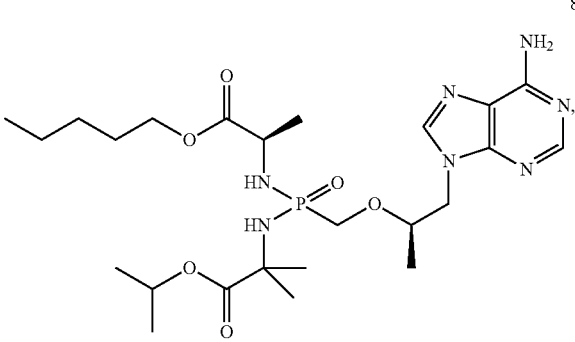
8
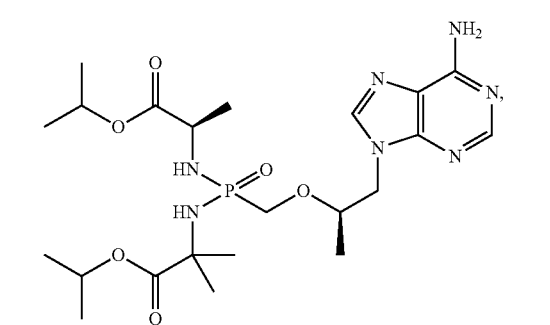
4
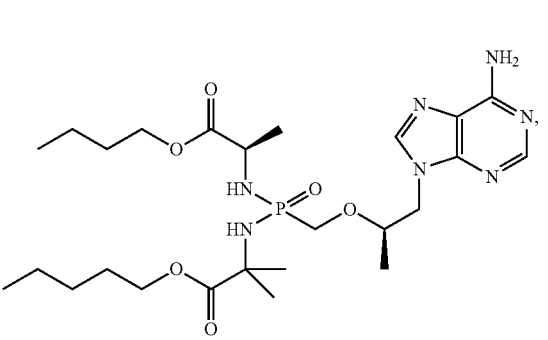
9
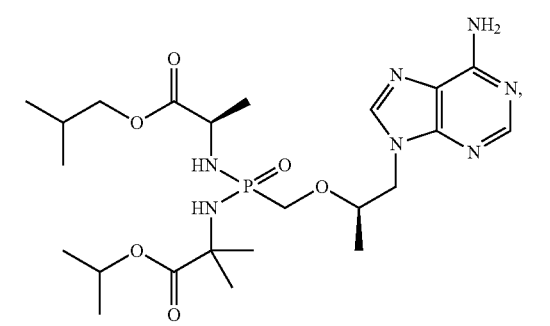
5
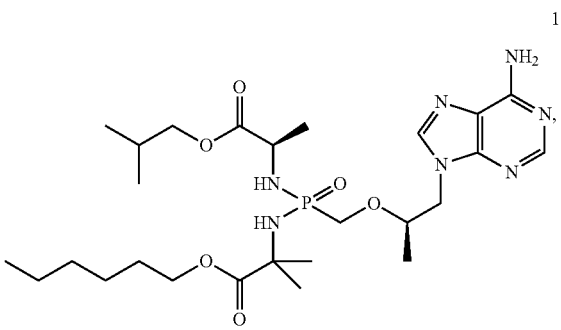
10
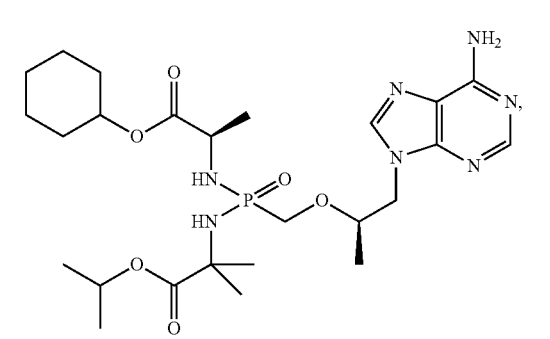
6
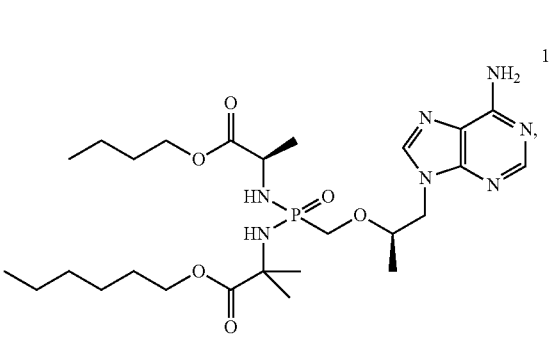
11

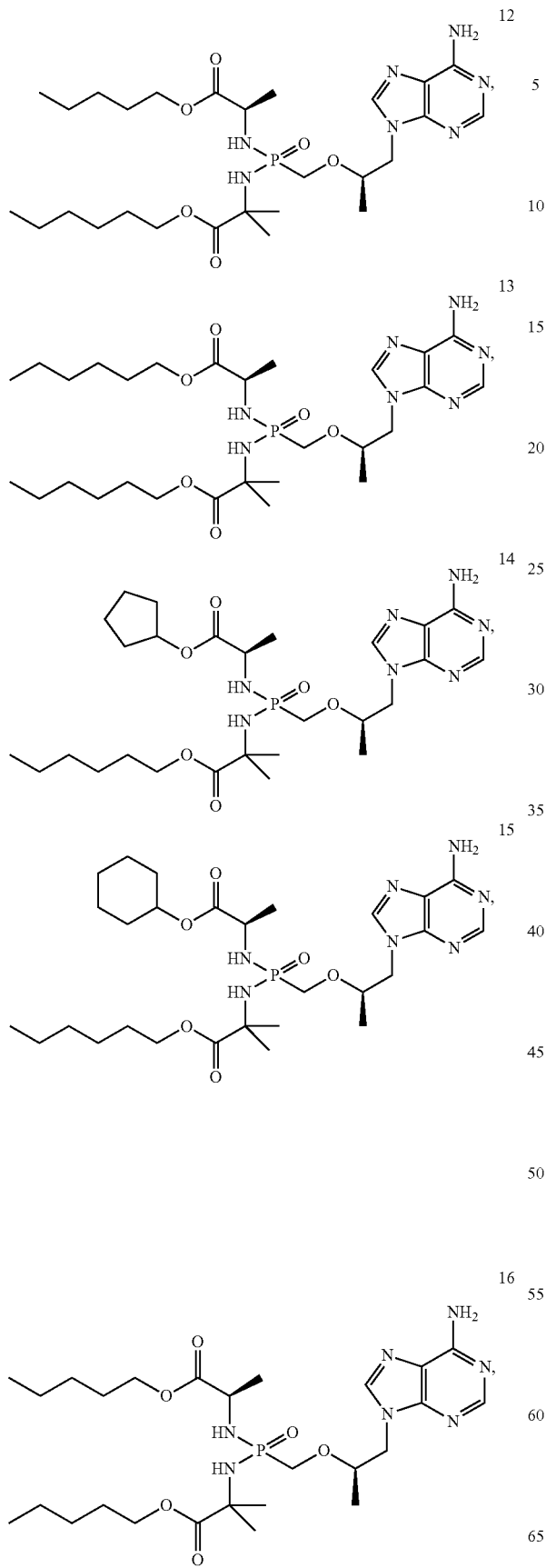
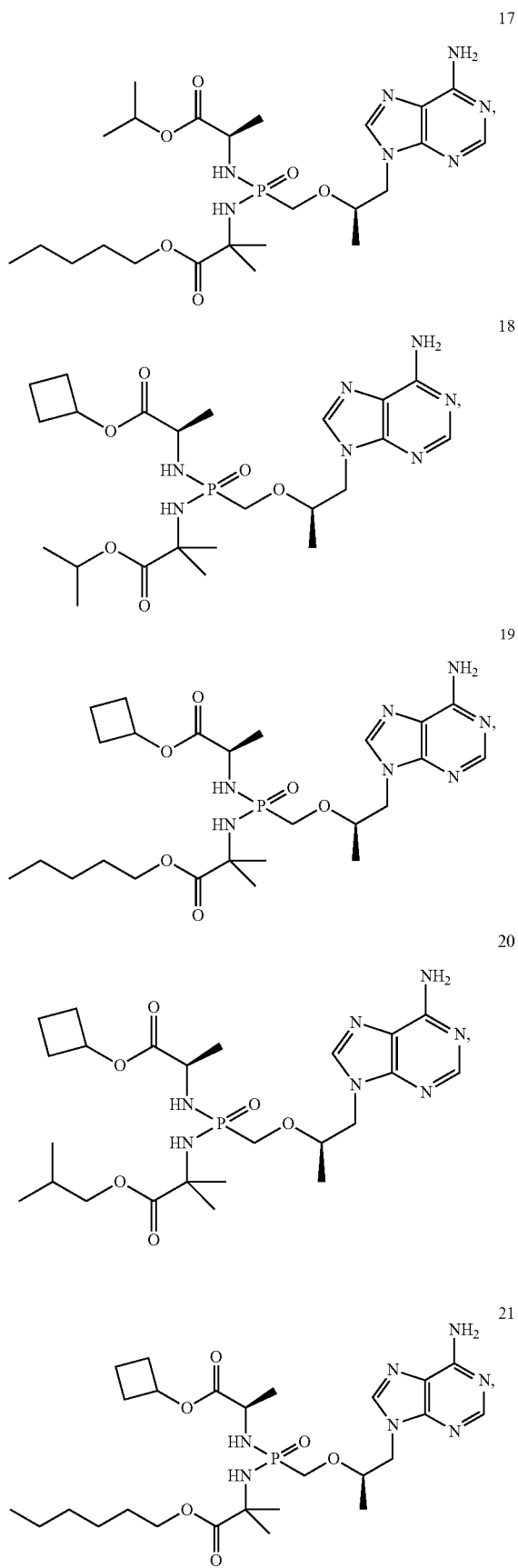

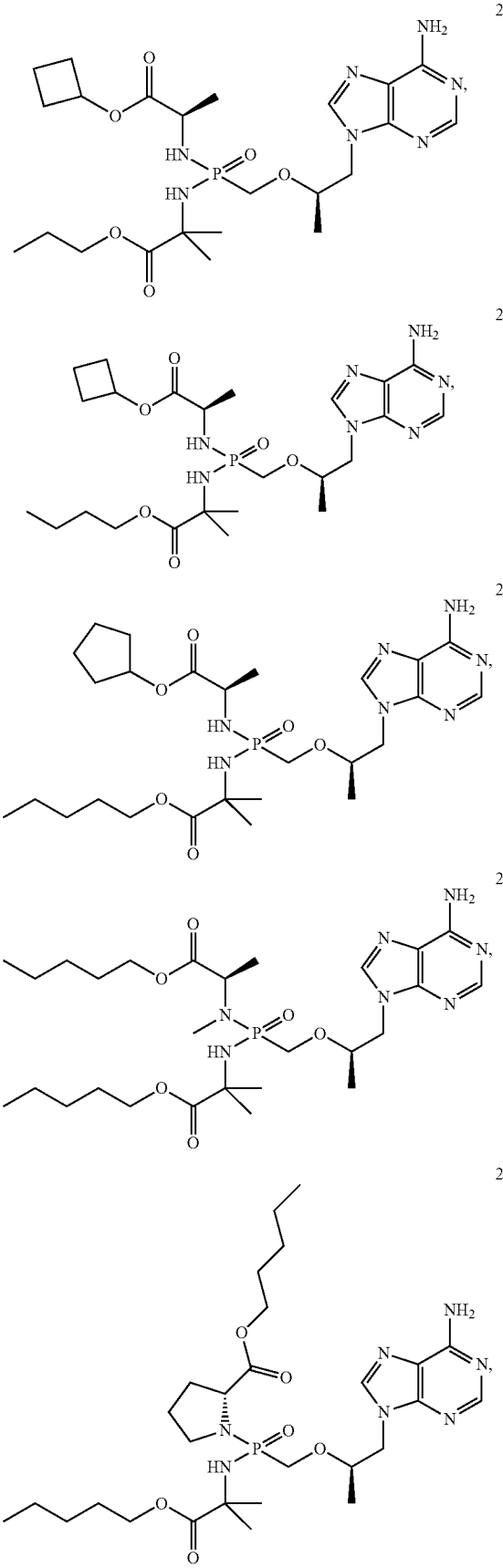
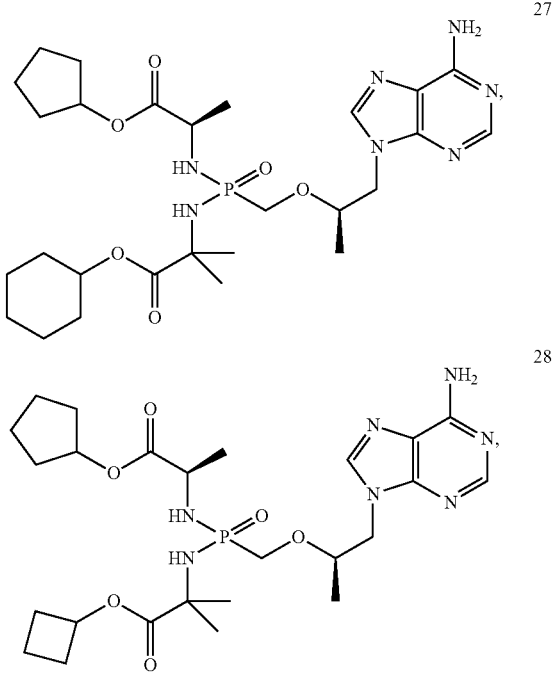

or a pharmaceutically acceptable salt thereof.

3. A compound which is selected from the following:

isopropyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;

isopropyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;

hexyl 2-(((S)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate;

hexyl 2-(((R)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate;

isopropyl 2-(((S)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate;

isopropyl 2-(((R)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate;

isopropyl 2-(((S)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate;

isopropyl 2-(((R)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate;

isopropyl 2-(((S)-((((R)-1-(6-amino-9H-purin-9-yl)propan-2-yl)oxy)methyl)(((R)-1-isobutoxy-1-oxopropan-2-yl)amino)phosphoryl)amino)-2-methylpropanoate;

isopropyl 2-(((R)-((((R)-1-(6-amino-9H-purin-9-yl)propan-2-yl)oxy)methyl)(((R)-1-isobutoxy-1-oxopropan-2-yl)amino)phosphoryl)amino)-2-methylpropanoate;

isopropyl 2-(((S)-((((R)-1-(6-amino-9H-purin-9-yl)propan-2-yl)oxy)methyl)(((R)-1-(cyclohexyloxy)-1-oxopropan-2-yl)amino)phosphoryl)amino)-2-methylpropanoate;

isopropyl 2-(((R)-((((R)-1-(6-amino-9H-purin-9-yl)propan-2-yl)oxy)methyl)(((R)-1-(cyclohexyloxy)-1-oxopropan-2-yl)amino)phosphoryl)amino)-2-methylpropanoate;
isopropyl 2-(((S)-((((R)-1-(6-amino-9H-purin-9-yl)propan-2-yl)oxy)methyl)(((R)-1-(hexyloxy)-1-oxopropan-2-yl)amino)phosphoryl)amino)-2-methylpropanoate;
isopropyl 2-(((R)-((((R)-1-(6-amino-9H-purin-9-yl)propan-2-yl)oxy)methyl)(((R)-1-(hexyloxy)-1-oxopropan-2-yl)amino)phosphoryl)amino)-2-methylpropanoate;
isopropyl 2-(((S)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate;
isopropyl 2-(((R)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate;
pentyl 2-(((S)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate;
pentyl 2-(((R)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate;
hexyl 2-(((S)-((((R)-1-(6-amino-9H-purin-9-yl)propan-2-yl)oxy)methyl)(((R)-1-isobutoxy-1-oxopropan-2-yl)amino)phosphoryl)amino)-2-methylpropanoate;
hexyl 2-(((R)-((((R)-1-(6-amino-9H-purin-9-yl)propan-2-yl)oxy)methyl)(((R)-1-isobutoxy-1-oxopropan-2-yl)amino)phosphoryl)amino)-2-methylpropanoate;
hexyl 2-(((S)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate;
hexyl 2-(((R)-((((R)-1-(6-amino-9H-purin-9-yl)propan-2-yl)oxy)methyl)(((R)-1-butoxy-1-oxopropan-2-yl)amino)phosphoryl)amino)-2-methylpropanoate;
hexyl 2-(((S)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate;
hexyl 2-(((R)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate;
hexyl 2-(((S)-((((R)-1-(6-amino-9H-purin-9-yl)propan-2-yl)oxy)methyl)(((R)-1-(hexyloxy)-1-oxopropan-2-yl)amino)phosphoryl)amino)-2-methylpropanoate;
hexyl 2-(((R)-((((R)-1-(6-amino-9H-purin-9-yl)propan-2-yl)oxy)methyl)(((R)-1-(hexyloxy)-1-oxopropan-2-yl)amino)phosphoryl)amino)-2-methylpropanoate;
hexyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;
hexyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;
hexyl 2-(((S)-((((R)-1-(6-amino-9H-purin-9-yl)propan-2-yl)oxy)methyl)(((R)-1-(cyclohexyloxy)-1-oxopropan-2-yl)amino)phosphoryl)amino)-2-methylpropanoate;
hexyl 2-(((R)-((((R)-1-(6-amino-9H-purin-9-yl)propan-2-yl)oxy)methyl)(((R)-1-(cyclohexyloxy)-1-oxopropan-2-yl)amino)phosphoryl)amino)-2-methylpropanoate;
pentyl 2-(((S)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate;
pentyl 2-(((R)-((((R)-1-(6-amino-9H-purin-9-yl)propan-2-yl)oxy)methyl)(((R)-1-oxo-1-(pentyloxy)propan-2-yl)amino)phosphoryl)amino)-2-methylpropanoate;
pentyl 2-(((S)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate;
pentyl 2-(((R)-((((R)-1-(6-amino-9H-purin-9-yl)propan-2-yl)oxy)methyl)(((R)-1-isopropoxy-1-oxopropan-2-yl)amino)phosphoryl)amino)-2-methylpropanoate;
isopropyl 2-((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
isopropyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
pentyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
pentyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
isobutyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
isobutyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
hexyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
hexyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
propyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
propyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
butyl 2-(((S)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
butyl 2-(((R)-((((R)-1-(6-amino-9H-purin-9-yl)propan-2-yl)oxy)methyl)(((R)-1-cyclobutoxy-1-oxopropan-2-yl)amino)phosphoryl)amino)-2-methylpropanoate;
pentyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;
pentyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;
pentyl 2-(((S)-((((R)-1-(6-amino-9H-purin-9-yl)propan-2-yl)oxy)methyl)(methyl ((R)-1-oxo-1-(pentyloxy)propan-2-yl)amino)phosphoryl)amino)-2-methylpropanoate;
pentyl 2-(((R)-((((R)-1-(6-amino-9H-purin-9-yl)propan-2-yl)oxy)methyl)(methyl((R)-1-oxo-1-(pentyloxy)propan-2-yl)amino)phosphoryl)amino)-2-methylpropanoate;
pentyl (((S)-(((R)-1-(6-amino-9H-purin-9-yl)propan-2-yl)oxy)methyl)((2-methyl-1-oxo-1-(pentyloxy)propan-2-yl)amino)phosphoryl)-D-prolinate;

pentyl (((R)-(((R)-1-(6-amino-9H-purin-9-yl)propan-2-yl)oxy)methyl)((2-methyl-1-oxo-1-(pentyloxy)propan-2-yl)amino)phosphoryl)-D-prolinate;

cyclohexyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;

cyclohexyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;

cyclobutyl 2-(((S)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;

cyclobutyl 2-(((R)-((((R)-1-(6-amino-9H-purin-9-yl)propan-2-yl)oxy)methyl)(((R)-1-(cyclopentyloxy)-1-oxopropan-2-yl)amino)phosphoryl)amino)-2-methylpropanoate;

a pharmaceutically acceptable salt thereof.

4. The compound of claim 2 which is

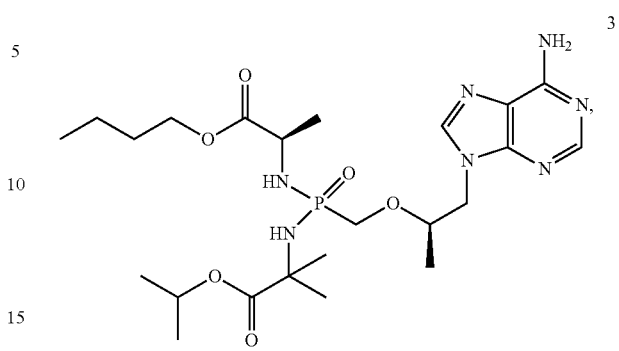

or a pharmaceutically acceptable salt thereof.

* * * * *